(12) United States Patent
Fuentes Garcia et al.

(10) Patent No.: US 9,066,956 B2
(45) Date of Patent: Jun. 30, 2015

(54) VAGINAL RING COMPRISING DHEA OR DHEA SULFATE AND OPTIONALLY A RELEASE-MODULATING AGENT OF THE ACTIVE PRINCIPLE, USEFUL TO INCREASE THE OVARIAN RESERVE IN WOMEN AND TO RELIEVE SYMPTOMS ASSOCIATED WITH MENOPAUSE

(75) Inventors: Frans Ariel Fuentes Garcia, Santiago (CL); Shu-Chen Chen, Santiago (CL); Marianela del Carmen Beltran Apablaza, Santiago (CL)

(73) Assignees: Universidad de Chile, Santiago (CL); Laboratories Andromaco S.A., Santiago (CL)

( * ) Notice: Subject to any disclaimer, the term of this patent is extended or adjusted under 35 U.S.C. 154(b) by 0 days.

(21) Appl. No.: 14/367,826

(22) PCT Filed: Dec. 29, 2011

(86) PCT No.: PCT/IB2011/056023
§ 371 (c)(1),
(2), (4) Date: Jun. 20, 2014

(87) PCT Pub. No.: WO2013/098592
PCT Pub. Date: Jul. 4, 2013

(65) Prior Publication Data
US 2015/0004214 A1    Jan. 1, 2015

(51) Int. Cl.
*A01N 43/76* (2006.01)
*A61K 31/42* (2006.01)
*A61K 31/5685* (2006.01)
*A61K 9/00* (2006.01)
*A61K 47/32* (2006.01)

(52) U.S. Cl.
CPC ........... *A61K 31/5685* (2013.01); *A61K 9/0036* (2013.01); *A61K 47/32* (2013.01)

(58) Field of Classification Search
USPC .......................................................... 514/374
See application file for complete search history.

(56) References Cited

U.S. PATENT DOCUMENTS

2002/0099003 A1    7/2002   Wilson et al.

FOREIGN PATENT DOCUMENTS

WO    2007070067    6/2007

OTHER PUBLICATIONS

Gleicher, N., et al., Dehydroepiandrosterone (DHEA) Supplementation in Diminished . . . , Reproductive Biology and Endocrinology, vol. 9, Article 67, pp. 1-12, 2011.
Casson, P.R., et al., Delivery of Dehydroepiandrosterone to Premenopausal Women . . . , American Journal of Obstetrics and Gynecology, vol. 174, No. 2, pp. 649-663, 1996.
International Search Report issued in PCT Application No. PCT/IB2011/056023.

*Primary Examiner* — Marcos Sznaidman
(74) *Attorney, Agent, or Firm* — Lucas & Mercanti, LLP

(57) ABSTRACT

Sustained-release vaginal ring for comprising dehydroepiandrosterone (DHEA), dehydroepiandrosterone sulfate (DHEA-S) or pharmaceutically acceptable thereof as active principle, and optionally a release-modulating agent of the active principle, wherein the amount of active principle is between 1% to 32% by weight, relative to the total weight of the formulation, and the modulator is selected from: polyvinylpyrrolidone K-30, lactose, microcrystalline cellulose and sodium lauryl sulfate. The vaginal ring of the present invention can be used to increase ovarian reserve in women, to be used as drug in assisted reproduction programs, and to relieve symptoms associated with menopause, such as symptoms of vulvar and vaginal atrophy and sexual dysfunction in postmenopausal women.

5 Claims, 13 Drawing Sheets

VAGINAL RING COMPRISING DHEA OR DHEA SULFATE AND OPTIONALLY A RELEASE-MODULATING AGENT OF THE ACTIVE PRINCIPLE, USEFUL TO INCREASE THE OVARIAN RESERVE IN WOMEN AND TO RELIEVE SYMPTOMS ASSOCIATED WITH MENOPAUSE

CROSS REFERENCE TO RELATED APPLICATION

This Application is a 371 of PCT/IB2011/056023 filed on Dec. 29, 2011 and the application is incorporated herein by reference in their entirety.

FIELD OF APPLICATION

The present invention relates to a vaginal ring containing dehydroepiandrosterone (DHEA) or dehydroepiandrosterone sulphate (DHEA-S) as active agent and optionally pharmaceutically acceptable excipients for modifying the release of the active agent, useful to increase the diminished ovarian reserve in women and to relieve symptoms associated with menopause, such as vulvar and vaginal atrophy and sexual dysfunction in women.

STATE OF THE ART

From the moment effective contraception was available, women have been postponing childbearing even to have their first child at an average age of 29-30 years, according to statistics in some European countries, in contrast with an average age between 23 and 25 in the early 1980s (Alviggi et al., 2009). Moreover, the reproductive capacity of women decreases over the years, beginning to decline at an average age of 30 years (Broekmans et al., 2009).

A combination of voluntary delay of first pregnancy and reduced natural fecundity with increasing age has resulted in a steady increase in the number of women over 35 years who are seeking for assisted reproductive technology (ART) treatment. These procedures highly complex and very expensive not always produce positive results. One of the most important factors that adversely affect these procedures is the advanced age of the patients, which is why improvements in these treatments are aimed at modifying the existing conditions in this group of women.

The usual therapy for infertile women is aimed to stimulate the ovaries, induce follicle development and oocyte release. It consists on pharmacological treatments with gonadotropins, and gonadotrophin-releasing hormone (GnRH), human menopausal gonadotropin (HMG), human chorionic gonadotropin (HCG) and follicle-stimulating hormone (FSH). Furthermore, it is possible to make pre-treatments with both estrogen and growth hormone (GH) in order to increase the action of gonadotropins. However, the clinical effects of ovarian stimulation are limited and responses have not been completely satisfactory. It is believed that with these treatments between 20 and 60% of women achieved pregnancy and of these between 70% and 85% would have an uncomplicated pregnancy, giving birth to a healthy baby. The patients not achieving good results can repeat treatments with gonadotropins, but only for a maximum period of 7 cycles.

In vitro fertilization (IVF) is one of the most widely used procedures in assisted reproductive technology. The procedure involves contacting woman eggs with man's spermatozoids. The first step is ovarian stimulation, oocytes are then retrieved through a puncture and the in vitro fertilization is performed in the laboratory, to finally transfer one or more of the resulting embryos to the uterus of the patient.

The treatment of ovarian stimulation with gonadotropins is also used as initial and fundamental part of the IVF protocol. It seeks to stimulate ovarian follicular development and achieve the release of oocytes for retrieval, under anesthesia, by aspiration of follicular fluid.

Poor ovarian response to gonadotropin stimulation is more common in women aged ≥35 years as the ovaries become less sensitive to FSH with increasing age (Alviggi et al., 2009). In turn, it also decreases the probability of embryo implantation and successful live birth after in vitro fertilization. In contrast, it has been observed that the outcome in patients using donor eggs remains relatively constant with increasing age, demonstrating that poor outcomes in older women relate to oocyte rather than to uterine factors.

Although chronological age is considered the most important parameter to project the ovarian response to FSH, the rate of reproductive aging varies considerably between individuals. Both environmental and genetic factors contribute to biological aging of the ovaries, so that chronological age and biological age are not always equivalent. Both older women and those with premature ovarian aging produce few oocytes and of these few are viable and normal (te Velde et al., 2002, Broekmans et al., 2009). Although ovaries are subjected to maximum stimulation with gonadotropins in IVF procedures, low oocyte production added to its lower quality is one of the major problems in IVF success.

Reproductive aging in women starts before birth through the transition to menopause, being the decrease in reserves of non-growing follicles in the ovaries (NGFs) the main mechanism occurring in this process. Folliculogenesis starts at 12 weeks of gestation and ends around week 21. At 4-5 months of fetal life, there are about of 6-7 million of oocytes surrounded by a granulosa cell layer to form the stock of primordial follicles. In the second half of fetal life, the apoptosis causes the loss of the vast majority of primordial follicles and at birth a woman has only 1 to 2 million of these follicles (Markström et al., 2002). The follicular loss continues at a slower rate after birth, reaching an endowment of about 400,000 follicles at menarche (te Velde et al., 2002).

The early models showed that the NGF decay rate follows an exponential and biphasic pattern with acceleration in the decay when the number of follicles falls below the critical level of 25,000 oocytes, which normally occur at about 38 years of age, to finally reach menopause with just one thousand oocytes (Faddy et al., 1992, Faddy at al., 1996). Subsequently, using new measurement and analysis technologies, it was shown that the decline of NGF is gradual through life without a sudden decay but with a consistent increase in the rate of follicular loss associated with aging (Hansen et al., 2008). This acceleration results in the number of follicles decays faster associated with aging.

More recently has been presented a model that relates NGF population in the human ovary from conception to menopause (Wallace et al., 2010). From this analysis it is estimated that 95% of women at the age of 30 years only have 12% of the maximum population of NGF that had before birth and at age 40 remains only 3% of the NGFs. They also found that the recruitment of NGF towards maturation phase increases from birth to the age of 14 and then decreases until menopause.

The population decline of NGFs is a continuous and physiological process that occurs along with the decline of ovarian quality of remaining oocytes (te Velde et al., 2002). It is thought that the stock NGFs is representative of the ovarian reserve (Hansen et al., 2008). The lower ovarian quality would be caused by an increase in the impossibility of meiotic division corresponding to abnormalities in the sister chromatids separation, which would cause an increased rate of aneuploidy in early embryos in older women (Battaglia et al., 1996 Kuliev et al., 2005, Pellestor et al., 2005, Hunt et al., 2008). As a result an increase in spontaneous abortions and chromosomal mutations in pregnancies after age 35 (Munne et al., 1995, Munne et al., 2005) is observed. Natural infertility can also occur prematurely in younger women. The change to a lower ovarian response is known as "diminished ovarian reserve" (DOR) or "diminished ovarian function" (DOF).

The primordial follicles are constantly being recruited, from before birth, to join the early growing follicle group. At this stage of early recruitment follicles are arrested at the first meiotic prophase. After puberty, a limited number of growing follicles are recruited in each new cycle (cyclic recruitment), and after a final selection, dominance and ovulation of a single follicle occurs (Gougeon 1996, McGee et al., 2000). At a certain point in life, most primordial follicles remain in a dormant state, and those that do not reach the preovulatory state, are destined to atresia in early stages of follicular development without reaching maturity and available to be ovulated. Only about 0.1% of the oocytes resumed meiosis upon stimulation with an increase in ovulation-inducing luteinizing hormone (LH) forming the haploid gamete available for fertilization.

The condition referred to as female infertility includes women who try and fail pregnancy over a period of 12 months (Evers, 2002). Many of these women are over 35 years old and suffering from a natural infertility. There are endocrine and ultrasound markers useful for estimating the ovarian biological age of individual patients and to help improve the personal attention, information and appropriate management of these patients. Among the markers include: FSH levels, antral follicle count (AFC), inhibin-B and anti-Müllerian hormone (AMH).

It has been shown that elevated baseline FSH levels are associated with a poor response to ovarian stimulation, which can be caused by a reduced number of oocytes leading to lower pregnancy rates when using assisted reproduction technologies (Abdalla et al., 2004, Alviggi at al., 2009). A poor response to ovarian stimulation is defined as antral follicle count (AFC) less than 5, wherein said follicles range in size between 2 and 5 mm (Klinkert et al., 2005).

AMH is a dimeric glycoprotein produced by granulosa cells of preantral and small antral follicles. Production begins when follicles differentiate from the primordial stage to the primary stage, and continues until the follicles have reached the middle antral stage with diameters between 2-6 mm. AMH production stops once the follicles have reached the dominant stage, which is the stage of FSH-dependent follicular growth (Ueno et al., 1989, Fanchin et al., 2003, Broekmans et al., 2009). Additionally, AMH disappears when the follicles reach the stage of atresia (Visser at al., 2006).

AMH is one or of the main regulators in the process of early follicle recruitment from the stock of primordial follicles (Durlinger et al., 2002). It has been shown that follicles are most sensitive to FSH and advance to early stages of follicle growth in absence of AMH (Durlinger et al., 1999, Durlinger et al., 2001). Once AMH is produced by the follicles in small growth, it has at least two sites of action in folliculogenesis, to inhibit initial follicular recruitment or to inhibit growth and selection of pre-antral follicles and FSH-dependent small antral follicles selection (van Houten, 2010).

Initially when serum AMH levels were detected, this hormone was postulated as a good indicator to detect tumor pathologies in male and female gonads (Hudson et al., 1990, Lee et al., 1996). Subsequently, AMH was visualized as a promising candidate to evaluate the ovarian aging (reviewed in Visser at al., 2006). As the quantitative aspect of this process is reflected by the decrease in the stock of primordial follicles, and as this stock is impossible to be directly measured, it can be estimated indirectly by the number of growing follicles (Scheffer et al., 1999), since the number of growing follicles is proportional to the size of the reserve of primordial follicles (Scheffer et al., 2003). For this reason, a factor mainly secreted by growing follicles, as AMH, will reflect the size of the stock of primordial follicles.

It has been observed that AMH serum levels gradually decline with increasing age, while expression of AMH in individual growing follicles does not change in mice. Serum AMH decrease correlates with the decrease in the number of growing follicles and mainly with primordial follicles decay (Kevenaar M E et al., 2006). Similarly, in adult women AMH serum levels decrease with increasing age to undetectable levels at menopause (Vet A et al., 2002, van Rooij et al., 2005). It has been shown that AMH levels do not change with menstrual cycle and not vary significantly between cycles (Fanchin at al., 2005, Hehenkamp et al., 2006), suggesting that AMH is not regulated by gonadotropins (van Houten ELAF et al., 2010).

AMH levels are closely correlated with the antral follicle count (AFC), and also with other markers of ovarian aging, such as FSH and inhibin B on day 3 of the cycle (Vet A et al., 2002). However, it has been observed that AMH levels decrease before than other markers do, resulting in the best indicator to predict the onset of menopausal transition (van Rooij et al., 2004). It was also observed that AMH is a better marker for predicting women reproductive age than chronological age (van at al., Disseldorp 2008).

Of the available markers to assess ovarian reserve, AMH levels constitute a reliable indicator to determine the condition of the ovaries, being a useful parameter for ART procedures. It has been demonstrated that AMH levels are closely correlated to antral follicle count (AFC), prior an ovulation induction treatment, and to the number of oocytes that are retrieved after treatment (van Houten ELAF et al., 2010). AMH levels are significantly lower in patients responding poorly to stimulation than those with a normal response (Seifer et al., 2002, van Rooij et al., 2002). Even though AMH is a good index for predicting ovarian reserve, has also been shown that this hormone has a low yield in predicting pregnancy, same as AFC (Broer et al., 2009). These results suggest that AMH is a good marker for quantitative ovarian reserve, not to assess ovarian quality. Nevertheless, there is a close relationship between AMH levels and number of oocytes retrieved. Others authors have found a direct relationship between high levels of AMH and good results of chemical pregnancy and clinical pregnancy by ART procedures, including IVF and intracytoplasmic sperm injection (ICSI) (Dehghani-Firouzabadi et al., 2008). In these studies, the good responders showed AMH levels considerably higher than poor responders. This response relates to the number of oocytes retrieved in the proceedings. In women with natural infertility, the low number of oocytes retrieved in IVF treatments is one of the major limitations on the success of the procedure, therefore, get this number increase from <4 (poor responders) to ≥4 (good responders) is an excellent result which could substantially amplify the probabilities of pregnancy in IVF.

Based on this background is imperative getting increase AMH levels in women that will undergo assisted reproduction programs.

Dehydroepiandrosterone (DHEA) and DHEA sulfate (DHEA-S) are steroids secreted in large amounts by the adrenal glands, which are converted into androstenedione or androstenediol and then, in peripheral tissues, into potent androgens and estrogens (Adams 1985, Labrie 1991). The serum DHEA and DHEA-S levels are the main source of androgens in women. Several reports have shown that aging women presents progressive decrease in serum levels of DHEA and DHEA-S from 30 years of age (Orentreich et al., 1984, Labrie et al., 1997). Among women of 50-60 years serum DHEA has decreased by 70% of the maximum value recorded at 20-30 years (Labrie et al., 1997). In circulation, DHEA-S can be metabolized to DHEA in peripheral and adrenal tissue by sulfohidrolases. It has been reported that 64% of the daily production of DHEA-S can be converted DHEA in women, but only 13% of DHEA is metabolized back to DHEA-S by sulfatase hydroxysteroid (reviewed in Kroboth at al., 1999). DHEA and DHEA-S are used as precursors for 75% of active estrogens in premenopausal women and for 100% at menopause (Labrie et al., 1997).

It has been observed that after administration of DHEA in rats, as vaginal suppositories, morphological changes in vaginal level indicating local conversion to active sex steroids having oestrogenic and/or androgenic action are produced (Labrie, 1991).

There are several scientific reports (Casson et al., 2000, Barad et al 2005, Barad et al., 2006, Barad at al., 2007, Sönmezer et al., 2009, Gleicher at al., 2009, Mamas et al., 2009, Gleicher et al., 2010a, Gleicher et al., 2010b, Gleicher et al., 2010c, Wiser et al., 2010) and patent documents (US20060089339, US2006089308, US2008269180, US2010048525 and US2010113407, US20110207708, U.S. Pat. No. 7,615,544) showing that administration of DHEA or DHEA-S improves production of the number of oocytes, the quality of them, the number and quality of embryos, improve the rates of spontaneous pregnancy, rates of IVF pregnancy, rates of cumulative pregnancy, time of conception and reduces spontaneous abortions.

The treatments described to increase ovarian reserve include oral administration of DHEA at a dose of 50 to 100 mg once a day for a period of one to four or more months. In the Patent Applications US2010048525 and US2010113407 those doses of DHEA are used orally, for at least one month to improve the ovarian reserve measured by changes in AMH serum levels. In these documents is described the assessment of women response to ovulation induction measured by the yield in the production of eggs and embryos by DHEA administration for a period of at least one month, more preferably for at least four months. The improvement of cumulative embryos count involving an improvement on quantity and quality of oocytes and embryos, and the improvement of rates of euploid embryos were also assessed. The effect is positive after two months of treatment but is improved even more if it continues for a period not less than 16 weeks. In addition, an increase in the number of oocytes fertilized with dose and duration of indicated treatments, an increased number of embryos on day 3, an increased number of euploid oocytes and number of embryos transferred was observed in women with diminished ovarian reserve. There was also an increase in DHEA levels, an increase in spontaneous conceptions, an increased in pregnancy rates and cumulative pregnancy, particularly in women who had diminished ovarian reserve.

It has been observed that DHEA administration resulted in increased basal levels of AMH in women receiving DHEA orally in daily doses for a period of between 30 to 120 days (US20100048525, US20100113407, US20110207708), and as the AMH has been suggested as a more specific marker for ovarian reserve, it has been used to evaluate the effect of DHEA in ovarian function. AMH measurements were performed before and after administration of DHEA, and it was found that serum AMH levels significantly improved as well as pregnancy success regarding the variation of AMH (Gleicher et al., 2010a).

In a study performed in 190 women (described in US20110207708, US20100048525, US20100113407), of which 89 had an average age of 41.6 years, 75 mg DHEA was used once daily or in three daily doses of 25 mg each, for a period of up to four months prior to the start of the IVF procedure. The other 101 women in the control group had an average of 40 years and received treatment for infertility but without using DHEA. The primary outcome was clinical pregnancy. They were subject to ovarian stimulation with HMG and FSH. The patients in the study group received DHEA until obtaining a positive test for pregnancy or until the patient completed treatment. Results were significantly higher in the study group with 28% of clinical pregnancies versus 11% in control group. Treatment with DHEA increased clinical pregnancy by at least 150% and also reduced the cumulative time of pregnancy. Moreover, the rate of spontaneous abortions was lower in the group treated with DHEA, being only 20% compared with 36% in the control group.

Results of clinical studies showing the effect of DHEA administration on spontaneous abortion rates in infertile women with diminished ovarian reserve, conducted in two independent fertility centers one in the U.S. and another from Canada are also described in U.S. Patent Applications US20100048525, US20100113407 and US20110207708. Results were compared with national rates of spontaneous abortions reported in the U.S. for IVF pregnancies in 2004. Reduction of spontaneous abortions was similar in both centers with a decreased of 15.0% and 15.2%, respectively. Differences were observed in all age groups but were more pronounced in women over 35 years. These results were also described in Gleicher et al., 2009.

To date, all treatments described to increase diminished ovarian reserve have used orally DHEA which implies daily administrations for long periods (from one to four or more months), with intakes that can be one to three times daily. Moreover, the additional inconvenience of oral DHEA administration is known, since it suffers a significant degradation in the liver, however is known for being well absorbed systemically after application on the skin and mucous membranes and has been found that therapeutically effective doses of DHEA can be administered transmucosally (ES2227523). With this type of administration the hepatic first-pass effect and discomfort of administration via injection would be avoided.

It is known that the vaginal route may have advantages in terms of reduced side effects and improved concentration of active compound at the site of interest. The rationale for this assertion lies in the concept of "first uterine pass" according to which the drugs administered vaginally preferably target pelvic organs. Mechanisms responsible for this flow directionality consist basically of passive absorption by simple osmosis, uterine peristalsis, and the extensive network of venous vessels around two thirds of the vagina that drain into the uterine isthmus and a special distribution of microcirculation around the uterus and annexes. The latter mechanism is called "of vascular counter-current" and consists of direct passage of solutes from the vein to the artery because of large surfaces in intimate contact and with opposing flows.

In the state of the art has been disclosed the use of vaginal ovules or vaginal suppositories comprising DHEA for the treatment of vulvar and vaginal atrophy, sexual dysfunction in postmenopausal women, and to alleviate other symptoms of menopause. Published International Patent Application WO2009021323 and reports by Labrie et al., 2008 and Labrie et al., 2009 are hereby incorporated by reference. These documents describes the use of DHEA in vaginal ovules at 3.25 mg (0.25%), 6.5 mg (0.5%), 13 mg (1.0%) and 23.4 mg (1.8%) doses, which are administered daily for periods ranging from one to twelve weeks for the treatment of the mentioned disorders.

Moreover, it has been found that vaginal preparations containing estrogen causes not only changes locally but increases in the systemic concentration, increasing the risk of side effects typical of estrogen (Beral V 2003, Heiss et al., 2008). There were no changes in the level of plasma estrogens with daily use of DHEA suppositories (Labrie et al., 2008), but serum levels remained within the values found in normal postmenopausal women, thus avoiding the increased risk of breast cancer found with the use of some preparations of estrogen intravaginal or systemically administered.

In the state of the art is possible to find the description of different pharmaceutical forms for administering DHEA or DHEA-S, as well as the use of these in the treatment or prevention of various diseases. Patent documents ES2227523, EP1350541, U.S. Pat. No. 5,948,434, U.S. Pat. No. 5,955,455, US2009054383, and ES2098193 are hereby incorporated by reference. These patents describe soft capsules for oral administration; cream, gel, ointment, lotion and patches for transdermal or percutaneous administration; ovules and suppositories for intravaginal administration. There is not description of vaginal rings comprising DHEA, only in patent document US2009054383 a ring is mentioned between various administration possibilities, but no particular vaginal ring is described.

The pharmaceutical industry has addressed the development of vaginal rings to supply different types of active principles, but only some of them comprising hormones have become part of the therapeutic arsenal for use in humans. This is because efficacy and safety have only been demonstrated for a few products in the form of vaginal rings, which has made them worthy of approval by the health authorities of different countries. These rings are used as contraception monotherapy (Progering®, progesterone), combination therapy (NuvaRing®, ethonogestrel and ethinylestradiol), hormone replacement therapy with estradiol for menopausal symptoms treatment (Estring®, Femring®), and as a luteal supplement in women requiring exogenous supply of progesterone for egg donation recipients in infertility cases, in vitro fertilization, embryo transfer and other assisted reproduction techniques (Fertiring®).

In U.S. Pat. No. 6,951,654 is mentioned that the drug is released from rings formed by a homogeneous or matrix design in which the active agent is homogeneously distributed in an elastomeric system, providing an exponential release decay, first order, characterized by a high initial release of drug followed by a slower release of drug, and it is stated that the drug cannot be released at a substantially constant or controlled (zero-order) release rate. U.S. Pat. No. 6,951,654 describes intravaginal drug delivery systems of substantially first order release during the first 24 hours, followed by at least three days of zero order release. Rings comprising an antimicrobial agent and agents that enhance the release of the active agent, such as polyvinylpyrrolidone, cellulose ethers, polyacrylic acid, carbomer, alginic acid, sugars such as lactose, cyclodextrins, among others are mentioned. Among the results showing cumulative drug release until day 25, is observed that at the same dose, 50 mg of metronidazole (MET), rings with 5% and 10% polyvinylpyrrolidone (PVP) released more amount of drug than rings without PVP over the 25 days period. Compared with higher doses different behavior is observed (U.S. Pat. No. 6,951,654, FIG. 3). In the first three days the release from vaginal rings containing PVP and 50 mg of metronidazole (MET) is slightly higher than from the rings containing higher dose of the active agent (100 mg MET) with no PVP. From day 6 begins to decrease the release from PVP rings, becoming lower than that of the systems that do not contain the agent (100 mg MET). From day 13, the cumulative release of the rings with PVP is significantly lower than from the rings with double dose but with no PVP. In U.S. Pat. No. 6,951,654 is observed that the addition of PVP or lactose to the rings induces higher release of antiseptics, but this increase is not sustainable over time and also does not exceed the highest dose release of the active principle, which does not comprise PVP, over time.

DETAILED DESCRIPTION OF THE INVENTION

There is a need for a sustained-release formulation that delivers DHEA or DHEA-S to be used in the treatment or prevention of diseases or disorders ameliorated by the use of DHEA, where said formulation is administered only once a month, once every two or three months, in order to facilitate long term therapies that are characteristic of DHEA therapeutic effect, and through a route of administration that allows to reduce or eliminate the effect of first-pass hepatic metabolism.

Formulation may comprise DHEA or its sulfated form, DHEA-S, since DHEA-S is converted endogenously into unsulfated form.

Formulation described in the present application relates to a sustained-release vaginal ring comprising DHEA or its sulfated form DHEA-S.

More preferably the present application is related to a sustained-release vaginal ring comprising DHEA or DHEA-S and a active principle release modifier.

In an even more preferred embodiment, the present invention relates to a sustained-release vaginal ring comprising DHEA or DHEA-S and a active principle release modifier, such as PVP K-30, lactose, microcrystalline cellulose or sodium lauryl sulfate.

With the sustained-release vaginal ring of the present invention is possible to obtain high tissue concentrations (local) and plasma levels that can be minimized or maximized depending on the presence of a modulating agent and the concentration used in the vaginal ring formulation, allowing to manage desired plasma levels of DHEA depending on the condition to be treated, treatment time and the target organs to be reached.

Additionally the use of a sustained-release vaginal ring comprising DHEA or DHEA-S as active agent, and optionally a active principle release modifier for the treatment or prevention of diseases or disorders which are improved with the use of DHEA is described.

More specifically, the present invention is related to the use of a sustained-release vaginal ring comprising DHEA or DHEA-S as active agent, and optionally a active principle release modifier for increasing ovarian reserve in women with diminished ovarian reserve.

Additionally, the present invention is related to the use of a sustained-release vaginal ring comprising DHEA or DHEA-S as active agent and optionally a active principle release modifier for treating symptoms associated with menopause Additionally, the present invention is related to the use of a sustained-release vaginal ring comprising DHEA or DHEA-S as active agent and optionally a active principle release modifier for treating vulvar and vaginal atrophy symptoms and sexual dysfunction in postmenopausal women.

More preferably a vaginal ring comprising DHEA or DHEA-S, and a drug release-enhancing agent, specifically PVP K-30, is presented. Surprisingly it has been found that administering vaginal rings with DHEA and PVP-K30, increases endometrial DHEA concentration without increasing plasma concentration of the drug at the same degree, compared with administration of a vaginal ring with the same concentration of DHEA but no PVP-K30. This ensures a therapeutic concentration in the target tissue while keeping low plasma concentrations, ensuring local therapeutic effect and decreasing the likelihood of undesired systemic side effects. This effect was not observed using other release-enhancing agents known in the state of the art. The PVP K-30 corresponds to the polymer of 1-vinyl-2-pyrrolidone, or polyvinylpyrrolidone, with a viscosity (or K value) between 26 and 35 centistokes in 1% solution.

EXAMPLES OF APPLICATION OF THE INVENTION

Example 1

Vaginal Rings Comprising DHEA or DHEA-S

Figure 1:
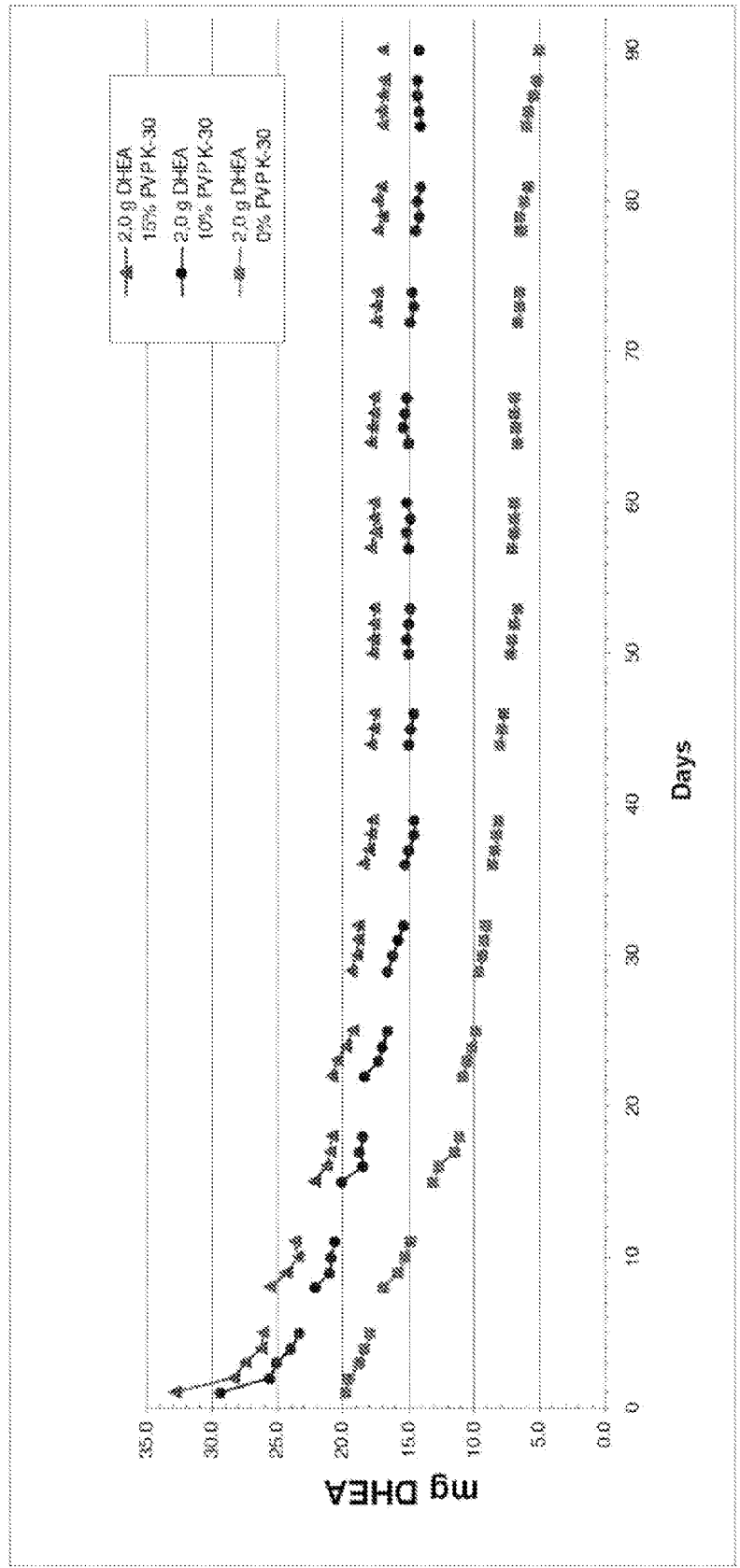
FIG. 1.—In vitro release profile of dehydroepiandrosterone (DHEA) from vaginal rings comprising 2.0 g of DHEA with no PVP K-30 or with 10% and 15% PVP K-30.

Vaginal rings comprising different amounts of DHEA or DHEA-S were made. A release-modulating agent of the active principle was added, the agent was selected from:
PVP K-30: Polyvinylpyrrolidone K-30 or polymer of 1-vinyl-2-pyrrolidone having a viscosity from 26 to 35 centistokes (K value between 26 and 35) in 1% solution
Sodium lauryl sulfate
Cremophor RH40: Ethoxylate hydrogenated castor oil (CAS 61788-85-0)
AA-1 polycarbophil: acrylic acid polymer crosslinked with divinyl glycol (CAS 9003-97-8)
Lactose
Microcrystalline cellulose.
1.1.—Formulations Tested
In Tables 1, 1a, 2 and 2a General Formulations (GF) tested are detailed. Polymers used together with various release modifiers are included.

TABLE 1

Vaginal rings formulations containing DHEA and PVP K-30

| | % W/W | | | | |
|---|---|---|---|---|---|
| INGREDIENT | GF-1 | GF-2 | GF-3 | GF-4 | GF-5 |
| Polymer A: Polydimethylsiloxane-vinyl block polymer + amorphous silica (25%) + platinum catalyst | 63.0-85.0 | 66.0-80.0 | 58.0-75.0 | 48.0-72 | 48.0-68.0 |
| Polymer B: Dimethyl methyl hydrogen siloxane copolymer (20%) + polydimethylsiloxane | 7.0-10.0 | 7.0-10.0 | 7.0-10.0 | 7.0-10.0 | 7.0-10.0 |
| DHEA | 5.0-30.0 | 5.0-25.0 | 5.0-30.0 | 3.0-35.0 | 2.0-30.0 |
| PVP K-30 | 0 | 2.0-5.0 | 5.0-10.0 | 10.0-15.0 | 15.0-20.0 |

TABLE 2

Vaginal rings formulations containing DHEA and release modifiers of the active principle other than PVP K-30

| INGREDIENT | GF-6 | GF-7 | GF-8 | GF-9 | GF-10 | GF-11 |
|---|---|---|---|---|---|---|
| | % W/W | | | | | |
| Polymer A: Polydimethylsiloxane-vinyl block polymer + amorphous silica (25%) + platinum catalyst | 62.9-84.0 | 61.0-80.0 | 55.0-77.0 | 53.0-72.0 | 57.0-77.0 | 0 |
| Polymer B: Dimethyl methyl hydrogen siloxane copolymer (20%) + polydimethylsiloxane | 7.0-10.0 | 8.0-10.0 | 8.0-10.0 | 7.0-10.0 | 6.0-7.0 | 0 |
| Polymer C: Polydimethylsiloxane with terminal hydroxyl group | 0 | 0 | 0 | 0 | 0 | 68.6-91.0 |
| Polymer D: Tetra-n-propyl-silicate $Si(OC_3H_7)_4$ | 0 | 0 | 0 | 0 | 0 | 1.0-3.0 |
| stannous octoate $Sn(C_8H_{15}O_2)_2$ | 0 | 0 | 0 | 0 | 0 | 0.2-1.0 |
| DHEA | 5.0-30.0 | 5.0-30.0 | 5.0-30.3 | 3.0-30.0 | 1.0-32.0 | 5.0-30.0 |
| Sodium lauryl sulfate | 0.1-1.0 | 0 | 0 | 0 | 0 | 0 |
| Cremophor RH40 | 0 | 1.0-5.0 | 0 | 0 | 0 | 0 |
| AA-1 Polycarbophil | 0 | 0 | 7.0-8.0 | 0 | 0 | 0 |
| Lactose | 0 | 0 | 0 | 10.0-15.0 | 0 | 0 |
| Microcrystalline cellulose | 0 | 0 | 0 | 0 | 5.0-15.0 | 0 |

Vaginal rings comprising the sulfated form of DHEA (DHEA-S), instead of DHEA, were also prepared as shown in Tables 1a and 2a.

TABLE 1a

Vaginal rings formulations containing DHEA-S and PVP K-30

| INGREDIENT | GF-12 | GF-13 | GF-14 | GF-15 | GF-16 |
|---|---|---|---|---|---|
| | % W/W | | | | |
| Polymer A: Polydimethylsiloxane-vinyl block polymer + amorphous silica (25%) + platinum catalyst | 63.0-85.0 | 66.0-80.0 | 58.0-75.0 | 48.0-72 | 48.0-68.0 |
| Polymer B: Dimethyl methyl hydrogen siloxane copolymer (20%) + polydimethylsiloxane | 7.0-10.0 | 7.0-10.0 | 7.0-10.0 | 7.0-10.0 | 7.0-10.0 |
| DHEA-S | 5.0-30.0 | 5.0-25.0 | 5.0-30.0 | 3.0-35.0 | 2.0-30.0 |
| PVP K-30 | 0 | 2.0-5.0 | 5.0-10.0 | 10.0-15.0 | 15.0-20.0 |

TABLE 2a

Vaginal rings formulations containing DHEA-S and active principle release modifier other than PVP K-30.

| INGREDIENT | GF-17 | GF-18 | GF-19 | GF-20 | GF-21 | GF-22 |
|---|---|---|---|---|---|---|
| | % W/W | | | | | |
| Polymer A: Polydimethylsiloxane-vinyl block polymer + amorphous silica (25%) + platinum catalyst | 62.9-84.0 | 61.0-80.0 | 55.0-77.0 | 53.0-72.0 | 57.0-77.0 | 0 |

TABLE 2a-continued

Vaginal rings formulations containing DHEA-S and active principle release modifier other than PVP K-30.

| INGREDIENT | % W/W | | | | | |
|---|---|---|---|---|---|---|
| | GF-17 | GF-18 | GF-19 | GF-20 | GF-21 | GF-22 |
| Polymer B: Dimethyl methyl hydrogen siloxane copolymer (20%) + polydimethylsiloxane | 7.0-10.0 | 8.0-10.0 | 8.0-10.0 | 7.0-10.0 | 6.0-7.0 | 0 |
| Polymer C: Polydimethylsiloxane with terminal hydroxyl group | 0 | 0 | 0 | 0 | 0 | 68.8-91.0 |
| Polymer D: Tetra-n-propyl-silicate Si(OC3H7)4 | 0 | 0 | 0 | 0 | 0 | 1.0-3.0 |
| stannous octoate Sn(C8H15O2)2 | 0 | 0 | 0 | 0 | 0 | 0.2-1.0 |
| DHEA | 5.0-30.0 | 5.0-30.0 | 5.0-30.0 | 3.0-30.0 | 1.0-32.0 | 5.0-30.0 |
| Sodium lauryl sulfate | 0.1-1.0 | 0 | 0 | 0 | 0 | 0 |
| Cremophor RH40 | 0 | 1.0-5.0 | 0 | 0 | 0 | 0 |
| AA-1 Polycarbophil | 0 | 0 | 7.0-8.0 | 0 | 0 | 0 |
| Lactose | 0 | 0 | 0 | 10.0-15.0 | 0 | 0 |
| Microcrystalline cellulose | 0 | 0 | 0 | 0 | 5.0-15.0 | 0 |

Various formulations assays were performed to obtain rings to adequately polymerize or cured with the necessary amounts of the active principle in the presence of a release-modulating agent. Rings containing Cremophor RH40 (General Formula 7, GF-7 and General Formula 18, GF-18) or polycarbophil (General Formula 8, GF-8 and General Formula 19, GF-19) did not cure, so that these agents were discarded. Other rings listed in Tables 1, 1a, 2 and 2a polymerized under assay conditions.

Manufactured rings had a weight between 6.0 to 10.5 grams, which varies according to ring thickness. Rings with outer diameter from 54 to 58 mm and cross section between 3 to 9 mm were fabricated.

1.2.—Procedure for Manufacturing Vaginal Rings

A homogeneous blend of all the ingredients to be injected into the ring molds was prepared. First the required amounts of each ingredient were weighed: Polymer A, release modifier agent, if applicable, and meloxicam. These ingredients were mixed until homogenization and the polymer B was added under constant mixing. The mixture was injected into ring molds at room temperature and then kept in an oven at 105° C. for 1 hour. Subsequently molds were cooled and the formed rings were disassembled from their respective molds obtaining the final product.

Rings were also made with other polymers, which were prepared by weighing each ingredient, as noted above, but replacing the polymer A with polymer B, and polymer C was replaced by polymer D, as indicated in Table 2 (GF-11) and 2a (GF-22). Additionally stannous octoate was added as catalyst for the polymerization reaction between polymers C and D. The ingredients were mixed until reaching homogeneity and were injected into ring molds. They remained at room temperature (23-25° C.) for 1 hour. The formed rings were then disassembled from their respective molds obtaining the final product.

1.3.—Preferred Formulations of the Present Invention

According to General Formulations of Tables 1 and 2, formulations of vaginal rings comprising different amounts of DHEA and drug release enhancers were prepared. Preferred formulations of the present invention are included in Tables 3, 4, 5 and 6. All ingredient amounts are expressed in grams.

TABLE 3

Pharmaceutical formulations of vaginal rings with DHEA containing PVP K-30

| Specific Formulas | Polymer A | Polymer B | DHEA | PVP K-30 |
|---|---|---|---|---|
| SF-1 | 8.5 | 1.0 | 0.5 | 0 |
| SF-2 | 8.0 | 1.0 | | 0.5 |
| SF-3 | 7.5 | 1.0 | | 1.0 |
| SF-4 | 7.0 | 1.0 | | 1.5 |
| SF-5 | 6.8 | 0.7 | | 2.0 |
| SF-6 | 8.0 | 1.0 | 1.0 | 0 |
| SF-7 | 7.5 | 1.0 | | 0.5 |
| SF-8 | 7.0 | 1.0 | | 1.0 |
| SF-9 | 6.5 | 1.0 | | 1.5 |
| SF-10 | 6.3 | 0.7 | | 2.0 |
| SF-11 | 7.0 | 1.0 | 2.0 | 0 |
| SF-12 | 6.5 | 1.0 | | 0.5 |
| SF-13 | 6.0 | 1.0 | | 1.0 |
| SF-14 | 5.5 | 1.0 | | 1.5 |
| SF-15 | 5.0 | 1.0 | | 2.0 |
| SF-16 | 6.5 | 1.0 | 2.5 | 0 |
| SF-17 | 6.0 | 1.0 | | 0.5 |
| SF-18 | 5.7 | 0.8 | | 1.0 |
| SF-19 | 5.0 | 1.0 | | 1.5 |

TABLE 4

Pharmaceutical formulations of vaginal rings with DHEA containing sodium lauryl sulfate (SLS)

| Specific Formulas | Polymer A | Polymer B | DHEA | SLS |
|---|---|---|---|---|
| SF-20 | 6.99 | 1.0 | 2.0 | 0.01 |
| SF-21 | 6.95 | 1.0 | | 0.05 |

TABLE 5

Pharmaceutical formulations of vaginal rings with DHEA containing lactose

| Specific Formulas | Polymer A | Polymer B | DHEA | Lactose |
|---|---|---|---|---|
| SF-22 | 7.1 | 0.9 | 1.0 | 1.0 |
| SF-23 | 6.6 | 0.9 |     | 1.5 |
| SF-24 | 6.1 | 0.9 | 2.0 | 1.0 |
| SF-25 | 5.6 | 0.9 |     | 1.5 |

TABLE 6

Pharmaceutical formulations of vaginal rings with DHEA containing microcrystalline cellulose

| Specific Formulas | Polymer A | Polymer B | DHEA | Microcrystalline cellulose |
|---|---|---|---|---|
| SF-26 | 7.7 | 0.7 | 1.0 | 0.5 |
| SF-27 | 6.7 | 0.7 |     | 1.5 |
| SF-28 | 6.7 | 0.7 | 2.0 | 0.5 |
| SF-29 | 5.7 | 0.7 |     | 1.5 |

The specific formulations (SF) listed in Tables 3 to 6 were also prepared using as active agent DHE-S in place of DHEA. All rings prepared according to the proportions shown in these tables polymerized appropriately.

Example 2

In Vitro Release Studies

In vitro release studies with the vaginal rings described in Tables 1 to 6 were performed according to the following analytical procedure. In the description of results for the formulations assayed nomenclature of Tables 3 to 6 will be used, as "SF-n", where n is the number of the formulation listed in these tables.

a) Diffusion medium preparation: 189 ml of Zephiran® (17% Benzalkonium chloride) were precisely measured, transferred to a polyethylene container with key containing 24 liters of distilled water. It was stirred to homogenize. The container was labeled assigning a preparation batch number and date of manufacture.

Once prepared diffusion medium, solution was checked by measuring absorbance at 262.4 nm, and the resulting reading should range between 1.3-1.6; otherwise the solution should be discarded.

b) Sample preparation: 4 rings of each formulation selected at random were individually weighed, taking note of the respective weight. Each of the rings was attached with a polyethylene thread of suitable length to allow submerge the rings completely. Rings were suspended in 500 mL wide-mouth polyethylene bottle with screw-cap (to prevent loss of diffusion medium); the rings were fixed with tape on the outer surface of the bottles, so that they were at 2, 0±0.2 cm from each bottle bottom. Bottles were labeled with its corresponding ring.

Bottles with samples were placed in a constant temperature water bath (BT-47 Model, Yamato, Japan), setting temperature at 37° C., and operating stirring system at 100 rpm. The bath temperature and stirring speed was checked every day. The temperature should be between 37±0.5° C. and the stirring speed within 100±5 rpm.

Medium solutions were change every day (after 24 hours), except on Sunday. From the second week Monday samples were discarded. Note that diffusion medium was replaced every day at the same time.

c) Analytical procedure: Prepared samples and taken samples are determined by UV spectrophotometry at 210 nm.

A calibration curve with different concentrations of micronized DHEA on diffusion medium was made in order to determine the range of concentrations that meets the Beer-Lambert Law. Standard concentrations to be prepared were defined, and, when necessary, samples dilutions were made.

d) Preparation of DHEA standard solutions: About 25 mg of micronized DHEA standard were precisely weighed, transferred to a 50 mL volumetric flask, about 25 mL of ethanol was added, dissolving and making up to volume with ethanol. The concentration of stock solution obtained was about 0.5 mg/ml. A 2.0 mL aliquot of stock solution was taken with a volumetric pipette to a 25 mL volumetric flask; volume was completed with diffusion medium used for measuring samples. The concentration obtained was about 0.04 mg/mL.

We proceeded to measure absorbance of taken samples and prepared standards at 210 nm.

The amounts of dehydroepiandrosterone released daily were calculated using the following formulas:

$$\text{Absorbance factor} = \frac{\text{Standard Concentration} \times \text{Diffusion Medium Volume (400 mL)}}{\text{Mean Standard Absorbance}}$$

$$\text{mg DHEA} = (\text{Absorbance Factor}) \times (\text{Sample Absorbance})$$

Results of in vitro release assays for vaginal rings comprising DHEA and a drug release modifier are described below.

2.1. Equal Doses of DHEA (2.0 g) at Different Concentrations of PVP K-30

FIG. 1 shows that the rings containing 2.0 g of DHEA in the absence of PVP K-30 (SF-11) had an mean initial release (day 1) of 19.8 mg of DHEA (see also Table 7). The initial release from rings containing 10% (SF-13) and 15% (SF-14) PVP K-30 was higher than in the absence of this agent, achieving mean values of 29.4 and 32.9 mg, respectively. Similarly, rings containing 5% PVP K-30 (SF-12) also had higher release than rings without this agent, achieving values of 23.6 mg (Table 7) on day 1 at equal dose of DHEA (2.0 g). During the first 4 days, the more pronounced release is maintained for rings with PVP K-30, although a quite pronounced initial decrease occurs in all cases (see FIG. 1).

In Table 7 are listed mean DHEA amounts released during the first 4 days from rings containing PVP K-30 at the listed concentrations. For each condition quadruplicate samples of release media of four rings were taken.

TABLE 7

Mean DHEA release from rings comprising 2.0 g of DHEA according to the Specific Formulas (SF) listed in Table 3

| | Mean DHEA release (mg) | | | |
|---|---|---|---|---|
| Days | SF-11 0% PVP K-30 | SF-12 5% PVP K-30 | SF-13 10% PVP K-30 | SF-14 15% PVP K-30 |
| 1 | 19.8 | 25.1 | 29.4 | 32.9 |
| 2 | 19.5 | 22.7 | 25.6 | 28.4 |
| 3 | 18.7 | 22.4 | 25.1 | 27.5 |
| 4 | 18.3 | 21.1 | 24.0 | 26.3 |
| Mean Release Days 1-4 | 19.1 | 22.8 | 26.0 | 28.8 |

Figure 5:
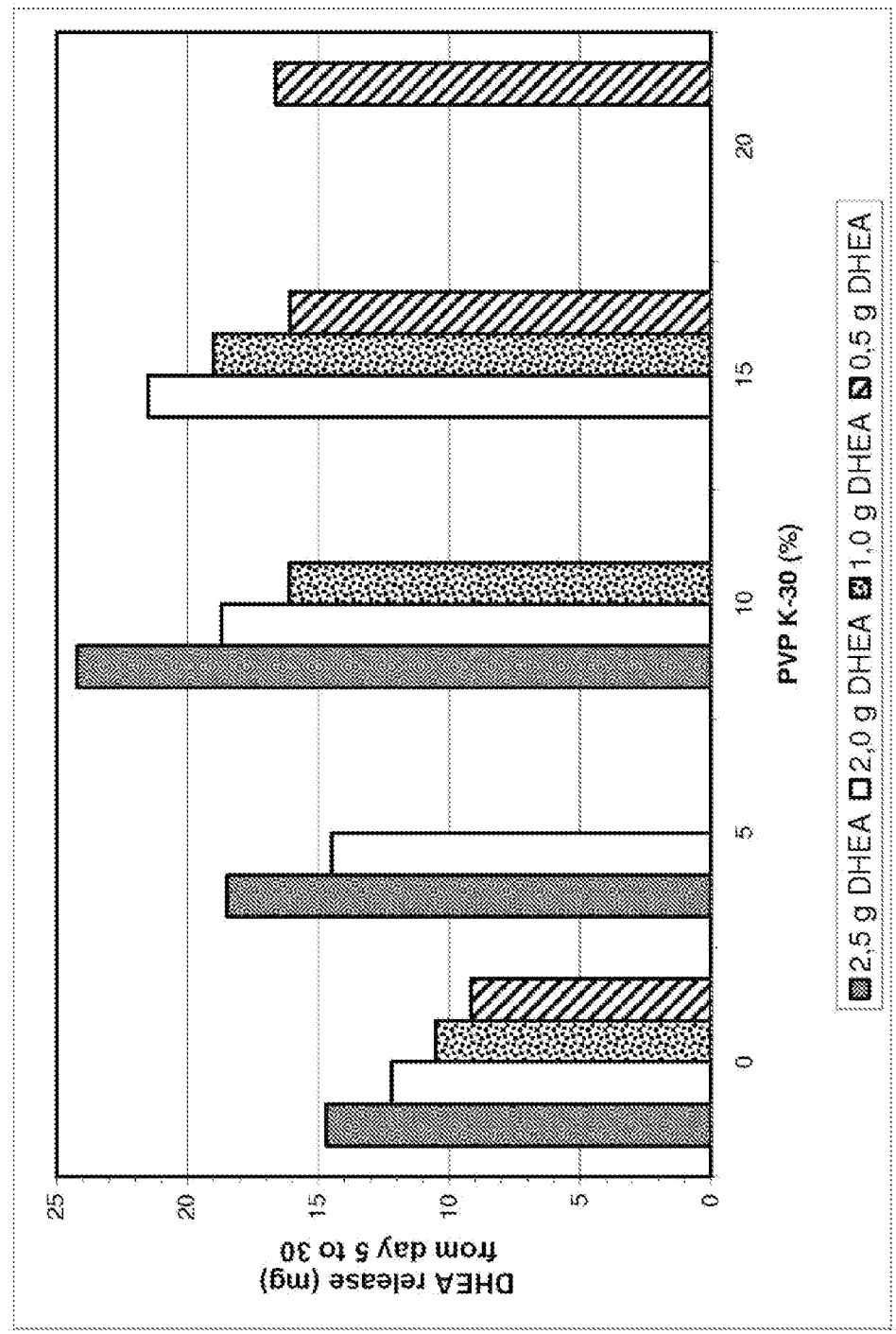
FIG. 5.—Mean in vitro release of dehydroepiandrosterone (DHEA) from day 5-30 from vaginal rings comprising 2.5 g, 2.0 g, 1.0 g and 0.5 g of DHEA with no PVP K-30 or with 5%, 10%, 15% and 20% PVP K-30.
Figure 6:
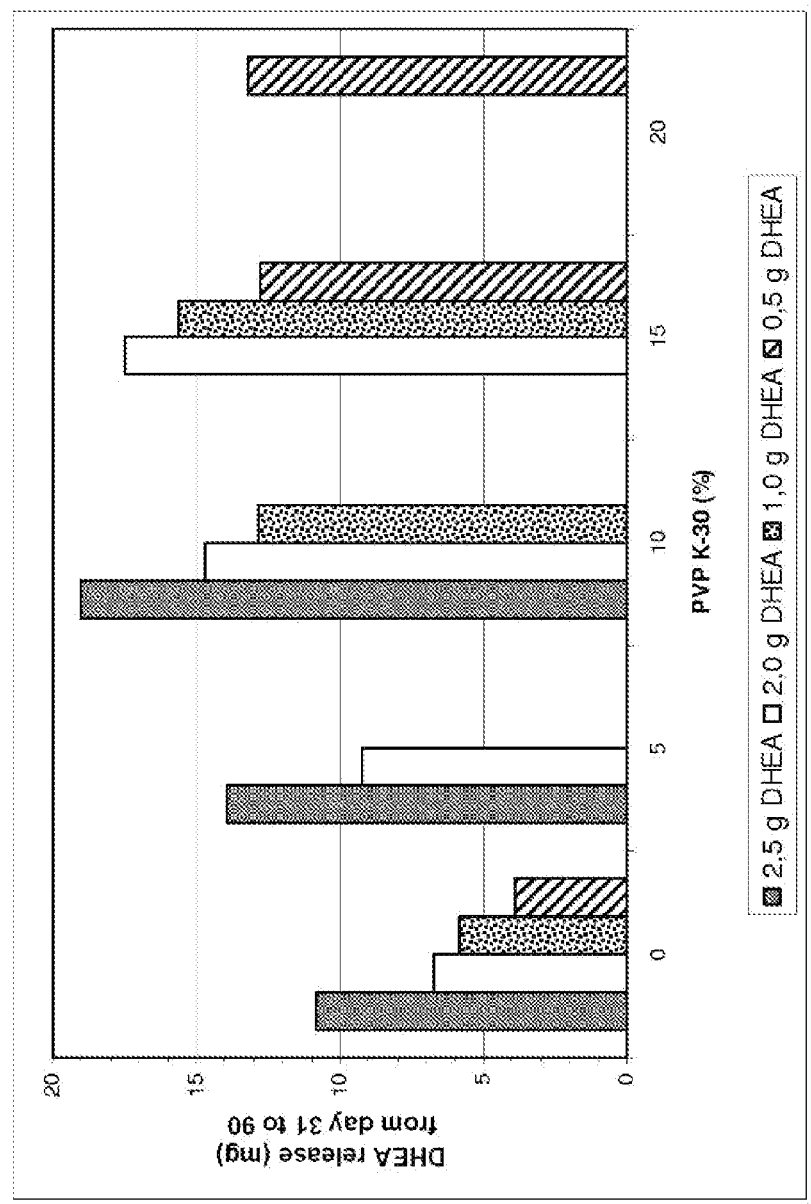
FIG. 6.—Mean in vitro release of dehydroepiandrosterone (DHEA) from day 31-90 from vaginal rings comprising 22.5 g, 2.0 g, 1.0 g and 0.5 g of DHEA with no PVP K-30 or with 5%, 10%, 15% and 20% PVP K-30.

From day 15, the slope of the release curve is much lower and the rings continue to release DHEA constantly and permanently over time, which is maintained until day 90. When comparing rings with equal doses of DHEA (2.0 g) with no PVP and with 10% and 15% PVP K-30 was also observed that the release of DHEA over extended periods of time was always higher in the rings containing PVP K-30, clearly evident from FIG. 1, being even higher in those rings with more amount of this agent. At 15% PVP K-30, the mean DHEA release between days 5-30 was 21.5 mg; whereas at 10% the mean was 18.7 mg, at 5% was 14.5 mg, and in the absence of PVP K-30 was 12.2 mg (FIG. 5, white bars). It is remarkable to observe that the release of DHEA remained even until 90 days maintaining the tendency observed in shorter periods of time; so it can be seen that mean DHEA release between days 31-90 in the presence of 15% PVP K-30 was 17.5 mg; whereas at 10% the mean was 14.7 mg, at 5% was 9.3 mg and in the absence of PVP K-30 was 6.7 mg (FIG. 6, white bars).

2.2.—Low Doses of DHEA in the Absence and Presence of Various Concentrations of PVP K-30

Figure 2:
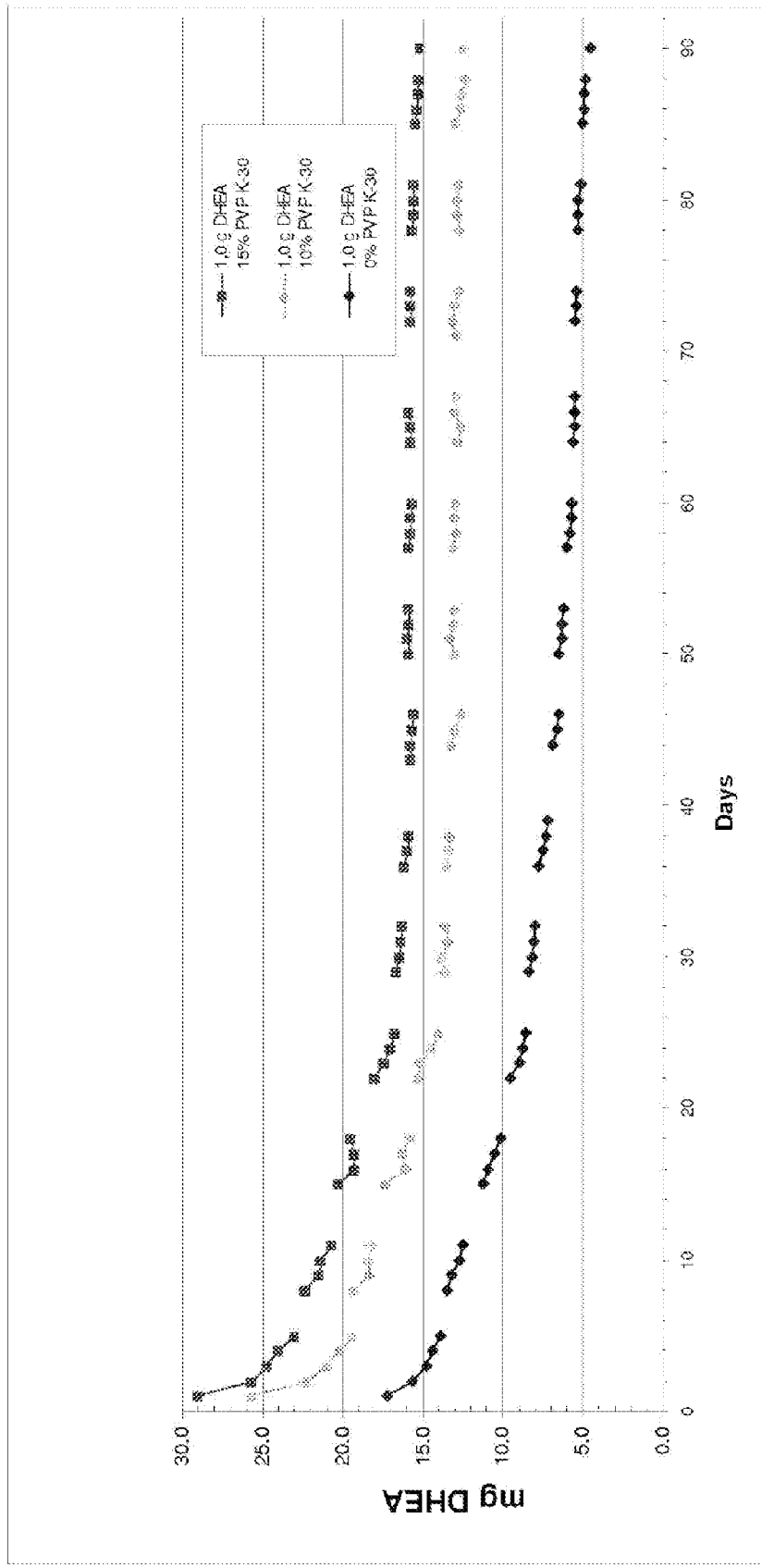
FIG. 2.—In vitro release profile of dehydroepiandrosterone (DHEA) from vaginal rings comprising 1.0 g of DHEA with no PVP K-30 or with 10% and 15% PVP K-30.
Figure 3:
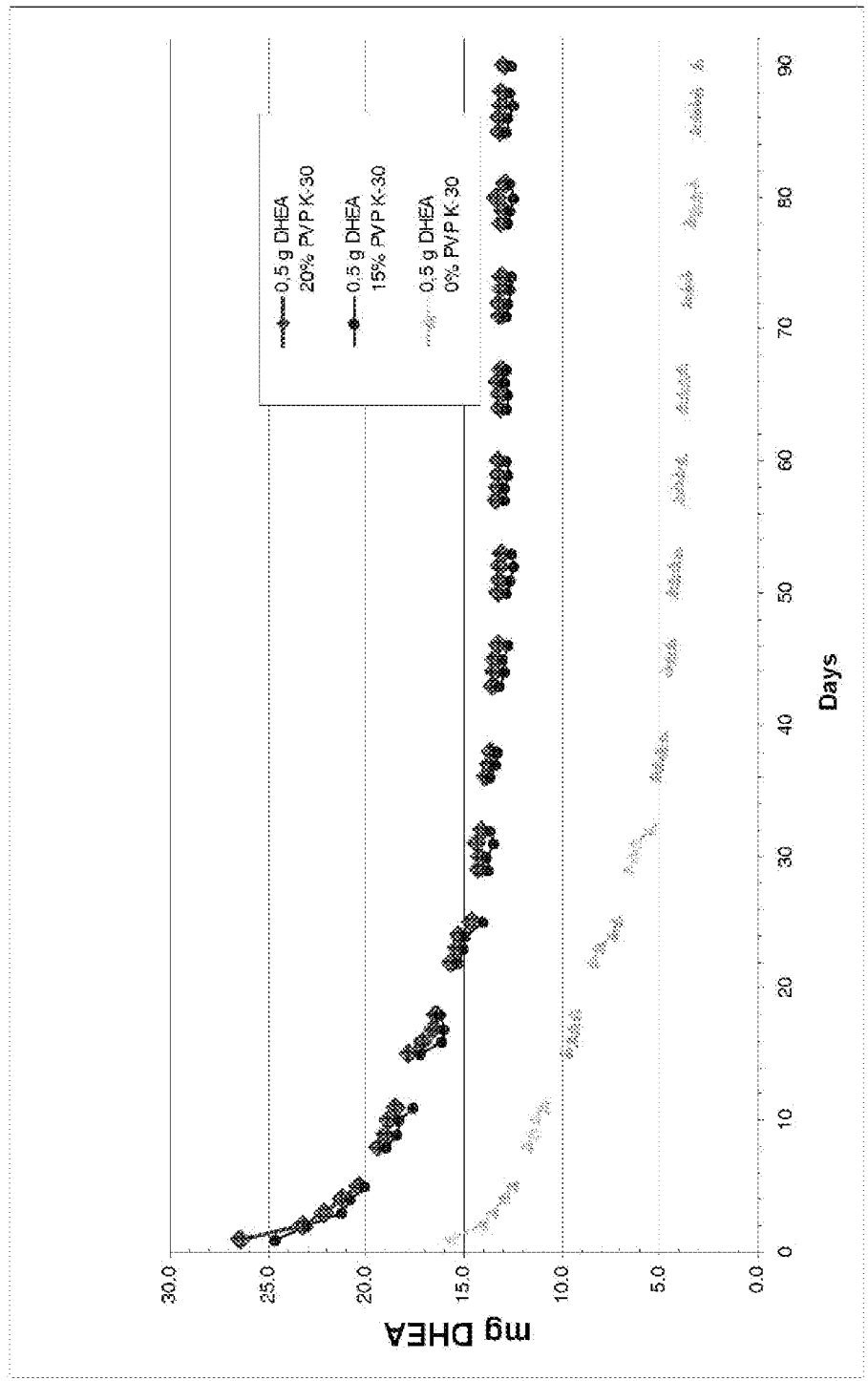
FIG. 3.—In vitro release profile of dehydroepiandrosterone (DHEA) from vaginal rings comprising 0.5 g of DHEA with no PVP K-30 or with 15% and 20% of PVP K-30.

At lower doses of DHEA (1.0 g, 0.5 g), the same effect of PVP K-30 was observed, i.e., the release of active principle was higher in those rings containing PVP K-30, increasing as agent concentration increased (FIGS. 2 and 3). Additionally, in rings with the lowest doses of DHEA (0.5 g) saturation of PVP K-30 effect was observed, as reflected in FIG. 3, where there was no clear difference in the release of DHEA for 15% (SF-4) (circles) and 20% (SF-5) (diamonds) of PVP K-30.

2.3.—High Doses of DHEA in the Absence and Presence of Various Concentrations of PVP K-30

Figure 4:
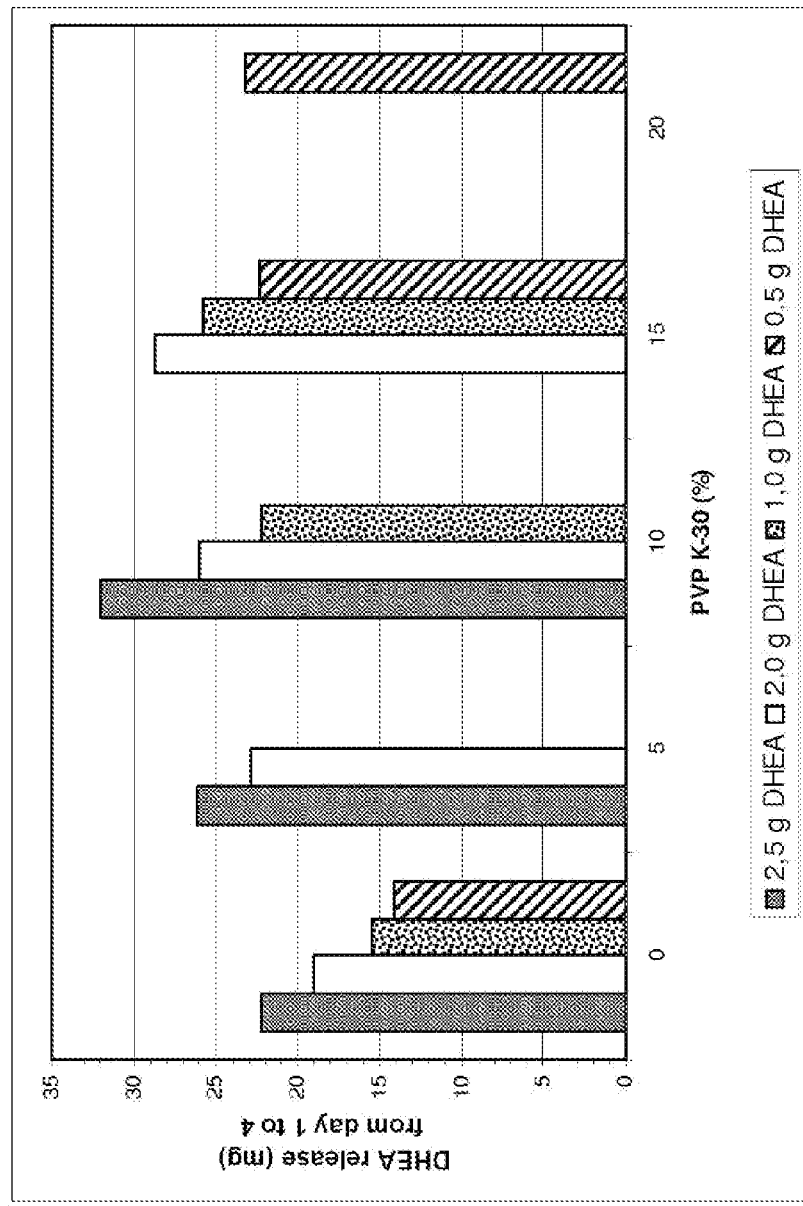
FIG. 4.—Mean in vitro release of dehydroepiandrosterone (DHEA) from day 1-4 from vaginal rings comprising 2.5 g, 2.0 g, 1.0 g and 0.5 g of DHEA, with no PVP K-30 or with 5%, 10%, 15% and 20% PVP K-30.

In addition, rings containing high doses of DHEA (2.5 g) in the absence (SF-16) and in the presence of PVP K-30 (SF-17 and SF-18) were assayed. In all cases the rings not containing PVP K-30 released a lower amount of DHEA throughout the test period. Between days 1 to 4, rings not containing PVP K-30 released 22.3 mg of DHEA, rings with 5% of PVP K-30 (SF-17) released 26.1 mg of DHEA and rings with 10% PVP K-30 (SF-28) released 32.1 mg of DHEA (FIG. 4, gray bars). In the following days (5-30 days), DHEA release also increased as PVP K-30 concentration increased, being 14.7 mg, 18.5 mg and 24.2 mg for 0%, 5% and 10% PVP K-30, respectively (FIG. 5, gray bars). Similarly, at longer times (31-90 days), a significant release of DHEA from these rings was still observed, achieving 10.8 mg, 4.0 mg and 19.1 mg for PVP K-30 concentrations of 0%, 5% and 10% (FIG. 6, gray bars).

Figure 7:
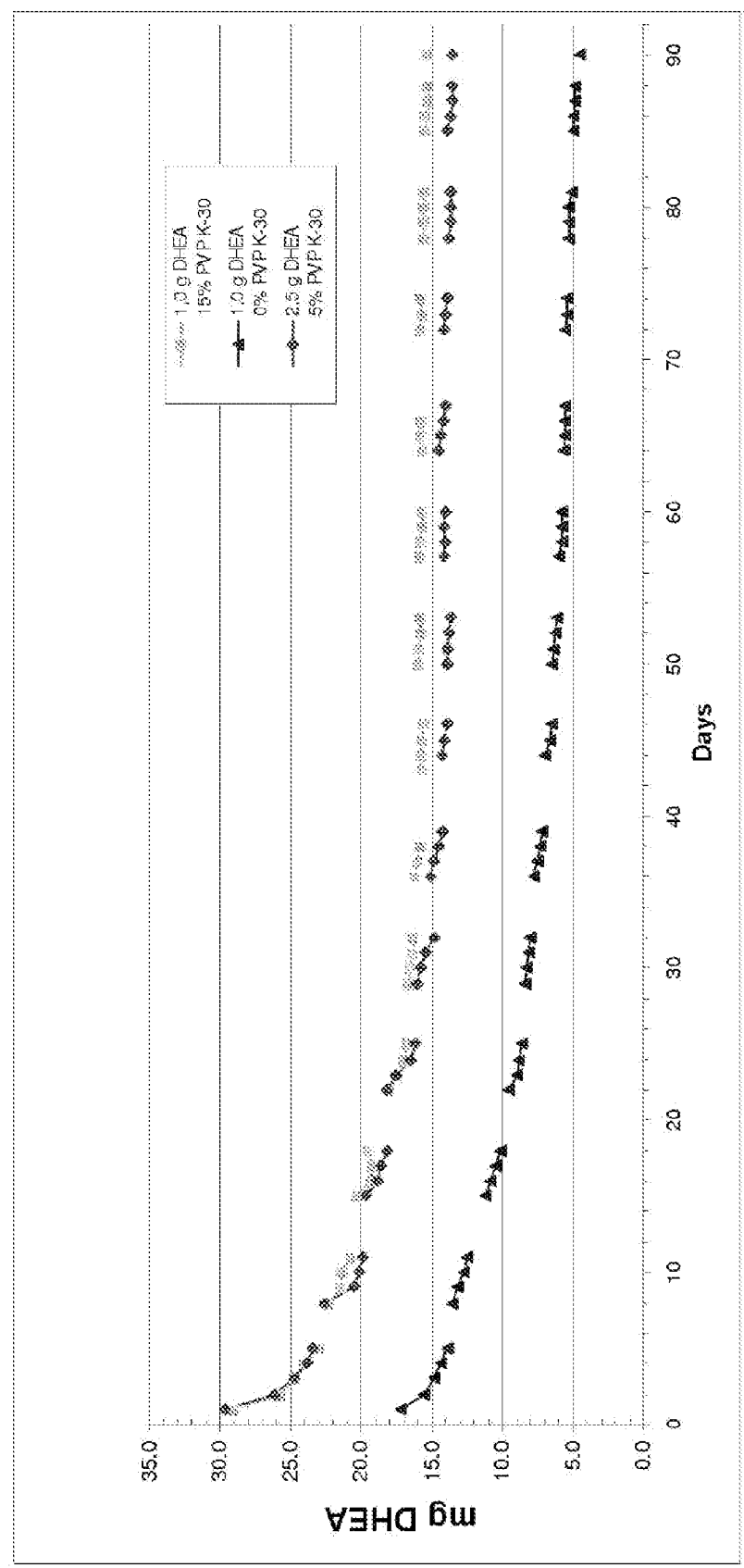
FIG. 7.—In vitro release profile of dehydroepiandrosterone (DHEA) from vaginal rings comprising 1.0 g of DHEA with no PVP K-30 and from rings comprising 1.0 g of DHEA with 5% PVP K-30, and 2.5 g of DHEA with 5% PVP K-30.

The dose of 2.5 g of DHEA was the highest dose assayed and accordingly was the dose with which a higher release of DHEA was obtained, with or without PVP K-30. The release obtained with 2.5 g of DHEA without PVP K-30 was achieved and exceeded by rings containing low doses of DHEA (1.0 g or 0.5 g) in the presence of 10% and 15% PVP K-30 (SF-9, Table 3) as shown in FIGS. 4-6 for all release times. In addition, the release obtained from rings with 2.5 g of DHEA and 5% PVP K-30 was achieved with rings comprising 1.0 g of DHEA and 15% PVP K-30, as seen in FIG. 7 where the release from rings with 1.0 g of DHEA in the absence of PVP K-30 (SF-6) (triangles) or in the presence of 15% PVP K-30 (SF-9) (squares) was compared with rings containing 2.5 g of DHEA and 5% PVP K-30 (diamonds).

Figure 8:
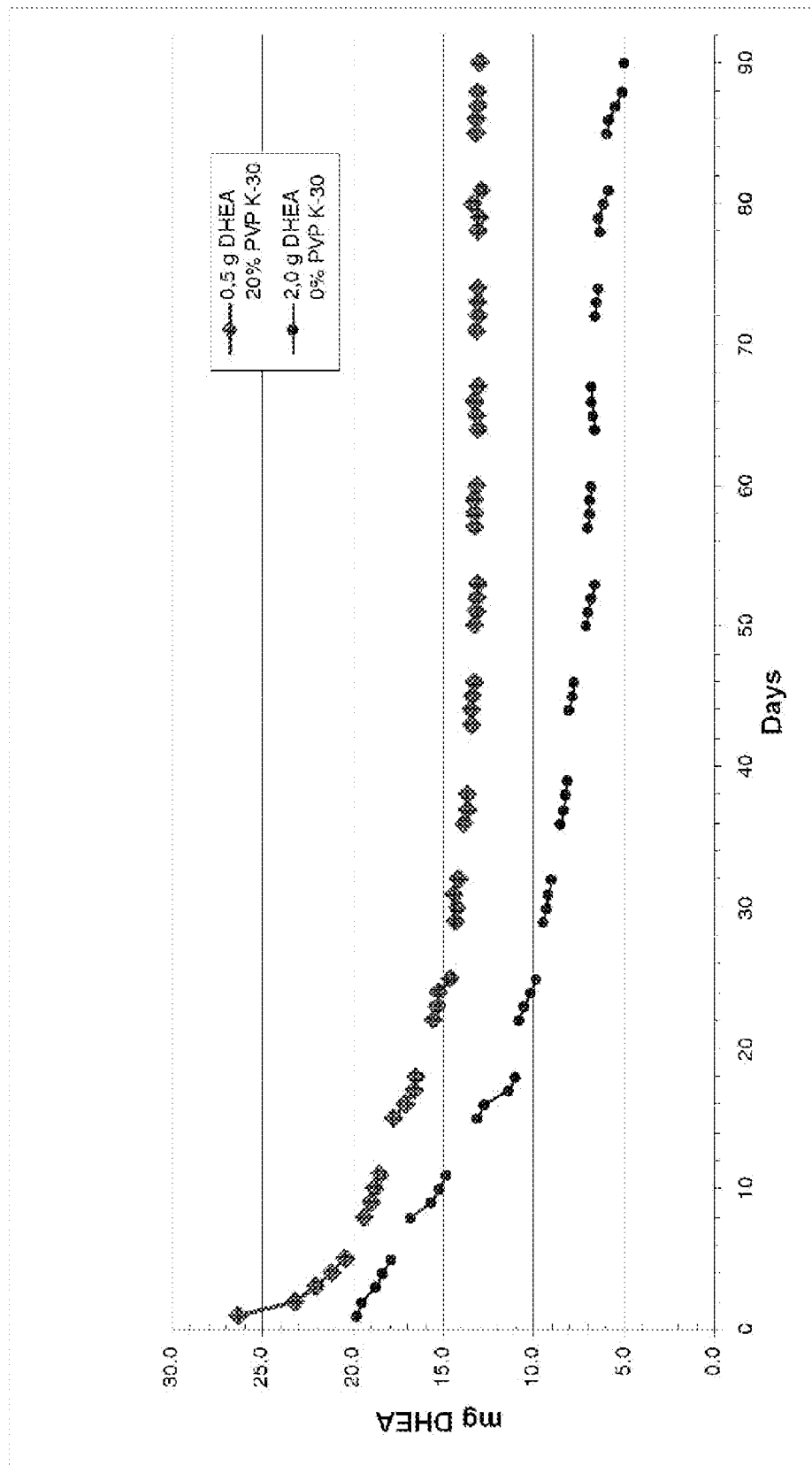
FIG. 8.—In vitro release profile of dehydroepiandrosterone (DHEA) from vaginal rings comprising 2.0 g of DHEA with no PVP K-30 and from rings comprising 0.5 g of DHEA with 20% PVP K-30.

Similarly, the level of release of the rings containing 2.0 g of DHEA with no PVP K-30 was lower than the release from rings containing lower doses of DHEA (0.5 g) with 20% PVP K-30 (SF-5), as seen in FIG. 8 and as compared in FIGS. 4, 5 and 6, white bars (0% PVP K-30) versus hatched bars (15% and 20% PVP K-30).

TABLE 8

| RING COMPOSITION | | | PHYSICAL PROPERTIES | | | | |
|---|---|---|---|---|---|---|---|
| DHEA (g) | Modulating agent | Modulating agent (%) | Consistency | Bright | Flexibility | Porosity | Stickiness |
| 0.5 | No | 0 | + | +++ | +++ | − | − |
| 0.5 | PVP K-30 | 15 | ++ | ++ | ++ | + | + |
| 0.5 | PVP K-30 | 20 | +++ | + | ++ | +++ | ++ |
| 1.0 | No | 0 | + | +++ | +++ | − | − |
| 1.0 | PVP K-30 | 10 | ++ | ++ | ++ | − | − |
| 1.0 | PVP K-30 | 15 | ++ | + | ++ | +++ | + |
| 2.0 | No | 0 | ++ | +++ | ++ | − | − |
| 2.0 | PVP K-30 | 5 | ++ | ++ | ++ | + | + |
| 2.0 | PVP K-30 | 10 | ++ | + | ++ | + | + |
| 2.0 | PVP K-30 | 15 | +++ | + | + | +++ | ++ |
| 2.5 | No | 0 | ++ | +++ | ++ | + | + |
| 2.5 | PVP K-30 | 5 | ++ | ++ | + | +++ | ++ |
| 2.5 | PVP K-30 | 10 | +++ | ++ | + | +++ | ++ |
| 2.0 (*) | No | 0 | +++ | ++ | + | +++ | ++ |

(*) These vaginal rings were prepared with polymer DDU 4340, according to General Formula 11 (GF-11) listed in Table 2

2.4.—Others Active Principle Release Modifiers

Figure 9:
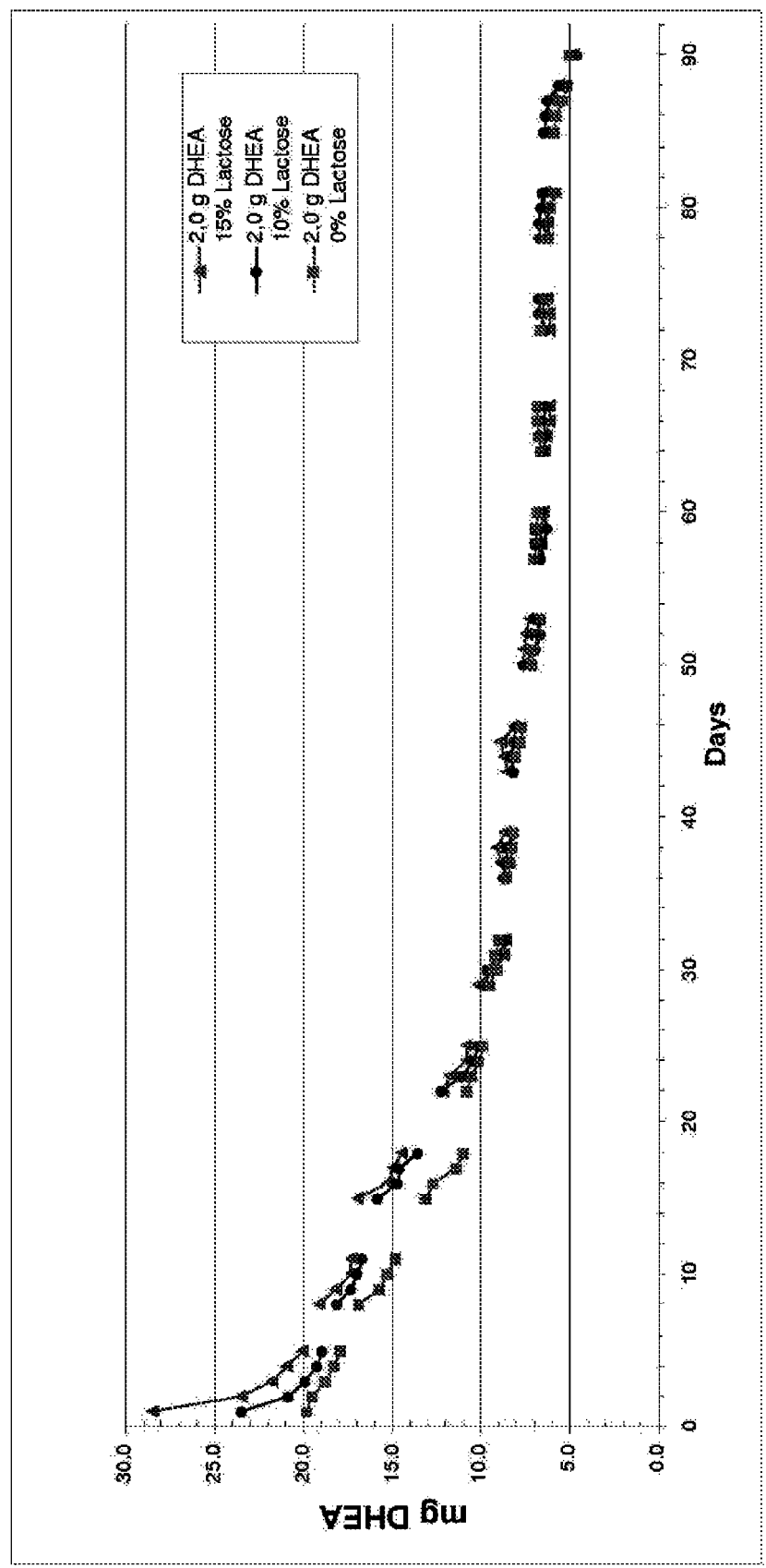
FIG. 9.—In vitro release profile of dehydroepiandrosterone (DHEA) from vaginal rings comprising 2.0 g of DHEA with no lactose or with 10% and 15% of lactose.

Rings containing DHEA at doses of 1.0 g 2.0 g with 10% of lactose (SF-22 and SF-24), 15% of lactose (SF-23 and SF-25), 5% of microcrystalline cellulose (SF-26 and SF-28) or 15% of microcrystalline cellulose (SF-27 and SF-29), released a higher amount of DHEA in short periods of time compared to rings containing DHEA but with no lactose or no microcrystalline cellulose; achieving the same release levels than the latter ones in longer periods of time. In FIG. 9 the effect of 10% and 15% of lactose producing an increased release of DHEA from the rings between days 1-22 was observed; but between days 23-90 release levels were indistinguishable between rings with and without lactose.

Figure 10:
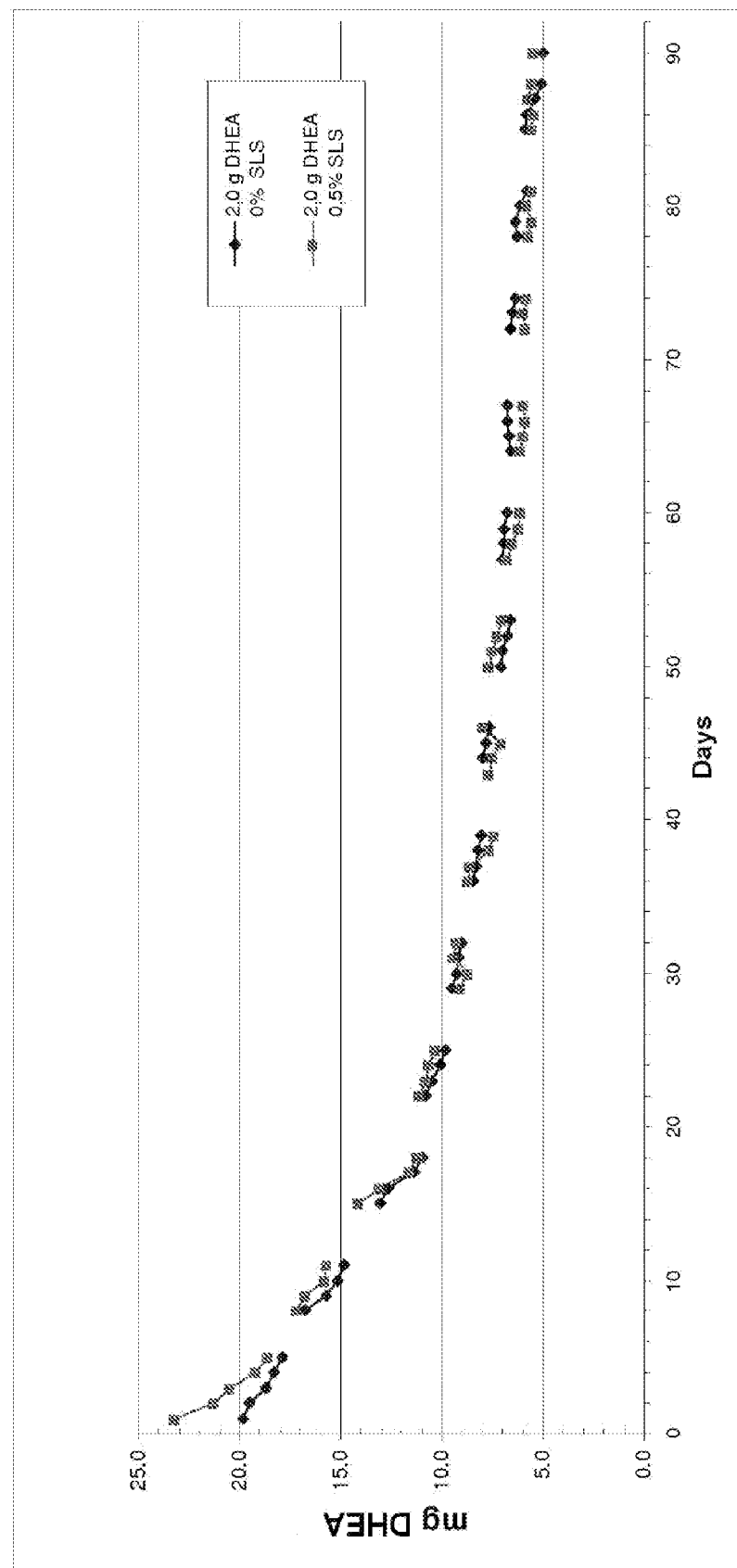
FIG. 10.—In vitro release profile of dehydroepiandrosterone (DHEA) from vaginal rings comprising 2.0 g of DHEA with no sodium lauryl sulfate (SLS) or with 0.5% of SLS.

Rings containing 2.0 g of DHEA with 0.1% (SF-20) or 0.5% (SF-21) of sodium lauryl sulfate (SLS), also released a higher amount of the drug than rings not containing SLS, but only in short periods of time (days 1-15). From day 16 to 90 no differences were observed between the rings with and without the agent, as shown in FIG. 10 for rings containing 0.5% of SLS and rings not containing SLS.

Higher concentrations of SLS were also assayed, but the rings did not properly cured so they were discarded.

From these results we conclude that only with PVP K-30 is possible to achieve a higher release of active principle compared with rings not having the agent both in short periods of time as in long periods of time (up to at least 90 days). With none of the tested agents a similar effect was obtained, either rings did not cured during polymerization step of manufacture or showed no differences of release at long periods of time.

The highest release of DHEA from rings containing PVP K-30 as a release-modulating agent was sustained over time even up to 90 days, being that release always higher than of those not containing this agent.

These results are completely surprising, as there was nothing that predicted the rings comprising PVP K-30 would present a release profile as observed, unlike all other agents tested.

2.5.—Other Polymers

Rings formed by Polymer C and D (see Table 2, GF-11) comprising different doses of DHEA and with no PVP K-30 were assayed. These rings were discarded as a product recommended for human use, because of the physical properties presented (see Table 8 and below). Nevertheless, the release profile of the rings containing DHEA was evaluated and it was observed that they release a higher amount of active principle throughout the recorded time, compared to rings made of Polymer A.

These results demonstrate that for a pharmaceutical product in the form of a vaginal ring is not enough that the rings exhibit an in vitro release profile with a high and stable active agent release rate, but it should also possess suitable physical characteristics, among others factors, to meet the requirements of acceptability of a finished product.

Example 3

Physical Properties of Rings

Vaginal rings comprising DHEA, in addition to possess the necessary releasing characteristics of the active principle to reach tissue levels allowing to achieve the therapeutic effect, must have other properties that make it suitable for intravaginal administration, besides certain acceptability requirements for users. Among these, the ring must be flexible so that the user can press it in order to give the necessary form to insert into the vagina. In addition, the ring must have a uniform smooth surface, smooth to the touch, without stickiness and regular consistency, i.e., with a certain softness to facilitate its application.

Rings were assayed at different doses of DHEA containing different release-modulating agents of the active principle at different concentrations. In these rings consistency (hardness), flexibility, porosity, stickiness and brightness properties were evaluated.

Rings comprising DHEA with PVP K-30, as a release modifier, had different physical properties depending on the concentration of this agent and the amount of DHEA in the ring. The addition of PVP K-30 gradually increased hardness (consistency), reducing flexibility and increasing the porosity of these. Furthermore, at high doses of PVP K-30 and DHEA rings stickiness markedly increased.

These observations are clearly seen in Table 8, where DHEA concentrations used with the release-modulating agent of the active principle are listed.

Correspondingly with the properties that intravaginal administration rings must possess, those with higher consistency were discarded, they had no brightness, were little or no flexible and were clearly porous and sticky. In consequence, rings comprising high concentrations of DHEA and/or PVP K-30 are not suitable for intravaginal administration, i.e., rings with 2.5 g of DHEA and 10% PVP K-30, rings with 2.0 g of DHEA and 15% PVP K-30 and rings with 0.5 g of DHEA and 20% PVP K-30 (Table 8).

The other release modifiers that were assayed also altered physical properties of the rings containing DHEA. Lactose containing rings showed similar consistency to that observed in the rings with PVP K-30 to the same doses of DHEA, as observed by comparing the data from Table 8 with Table 9. Flexibility of the rings containing 2.0 g of DHEA and lactose was much lower than that of the rings containing 1.0 g of DHEA with the same agent (10% or 15%). Rings with lactose had high porosity and a low level of brightness and stickiness. Considering only physical properties rings containing high doses of DHEA (2.0 g) and lactose (15%) are not recommended as final product (Table 9).

Rings with DHEA and 0.5% microcrystalline cellulose had physical properties of consistency, flexibility, stickiness and brightness suitable for being administered transvaginally, although they had a certain degree of porosity. Rings with high-dose of microcrystalline cellulose (15%) were not recommended as final product by its high consistency (hardness) and high porosity (rough surface) (Table 9).

Rings containing 2.0 g of DHEA and 0.1% or 0.5% of sodium lauryl sulfate (SLS) were also assayed. Under both conditions the rings had good physical properties (Table 9), therefore considering only these parameters, they would be recommended as a final product.

TABLE 9

| RING COMPOSITION | | | PHYSICAL PROPERTIES | | | | |
|---|---|---|---|---|---|---|---|
| DHEA (g) | Modulating agent | Modulating agent (%) | Consistency | Bright | Flexibility | Porosity | Stickiness |
| 1.0 | Lactose | 10 | ++ | ++ | +++ | + | + |
| 1.0 | Lactose | 15 | +++ | + | ++ | ++ | + |
| 2.0 | Lactose | 10 | ++ | + | + | ++ | + |
| 2.0 | Lactose | 15 | +++ | + | + | +++ | + |
| 1.0 | Microcrystalline cellulose | 5 | ++ | + | ++ | ++ | − |
| 1.0 | Microcrystalline cellulose | 15 | +++ | + | + | +++ | + |
| 2.0 | Microcrystalline cellulose | 5 | ++ | ++ | ++ | +++ | + |
| 2.0 | Microcrystalline cellulose | 15 | +++ | + | + | +++ | + |
| 2.0 | SLS | 0.1 | ++ | ++ | ++ | + | − |
| 2.0 | SLS | 0.5 | ++ | + | ++ | + | − |

In addition, alternative polymers used for rings manufacturing (polymers C and D, as defined in Table 2) also affected the physical properties thereof. In the manufacturing process when injecting molds was observed that the mixture containing these polymers was remarkably more consistent and viscous than the mixtures with the other polymers (polymers A and B), making difficult injecting and filling the molds because of the pressure that had to be exerted. The rings polymerized (cured) but were very rigid, hard and poor flexibility, making it difficult to keep them folded simulating the condition of intravaginal application. Therefore, because of the high consistency (hardness), poor flexibility, certain porosity and stickiness (Table 8), these rings are not suitable as a final product.

Example 4

DHEA In Vivo Release Studies

For evaluating vaginally release and absorption of DHEA in vivo, three vaginal rings with different formulations were administered in nine healthy women volunteers over 38 years old. Endometrial and plasma levels of the active agent after administration of DHEA containing rings with or without the modulating agent were measured.

The rings used in this study contained: 1) 1.0 g de DHEA with no modulating agent; 2) 2.0 g of DHEA with no modulating agent; y 3) 1.0 g of DHEA plus 15% PVP K-30. Each one if these rings were administered in three volunteers. These doses of active and modulating agents were chosen for studies in vivo because in vitro release studies showed a marked difference between them in the amount of DHEA released throughout the recorded period time (1-90 days), and also by the excellent physical properties of the respective rings. All these features made them recommendable as potential final products.

Women installed vaginal rings on day 3-5 of their menstrual cycle or after heavy menstrual bleeding ended. Blood samples were taken from each volunteer at the following times (in hours time post-administration of the ring): 1, 2, 6, 24, 72, 120, 168, 216, 360, 372, 528 and 720. Endometrial fluid samples were also taken on days 3, 7, 15 and 22 post-administration of the ring. Volunteers were told that the ring could remain installed during the next menstrual cycle, but it could be removed if it cause discomfort for heavy flow.

Data of plasma levels at 720 hours (30 days) of the volunteers that had to remove the vaginal ring were discarded. Two volunteers, one from Group 1 and one from Group 3 removed the ring. The other women kept the ring installed for at least 60 days. The results obtained up to 30 days were analyzed in order to standardize the evaluation.

Figure 11:
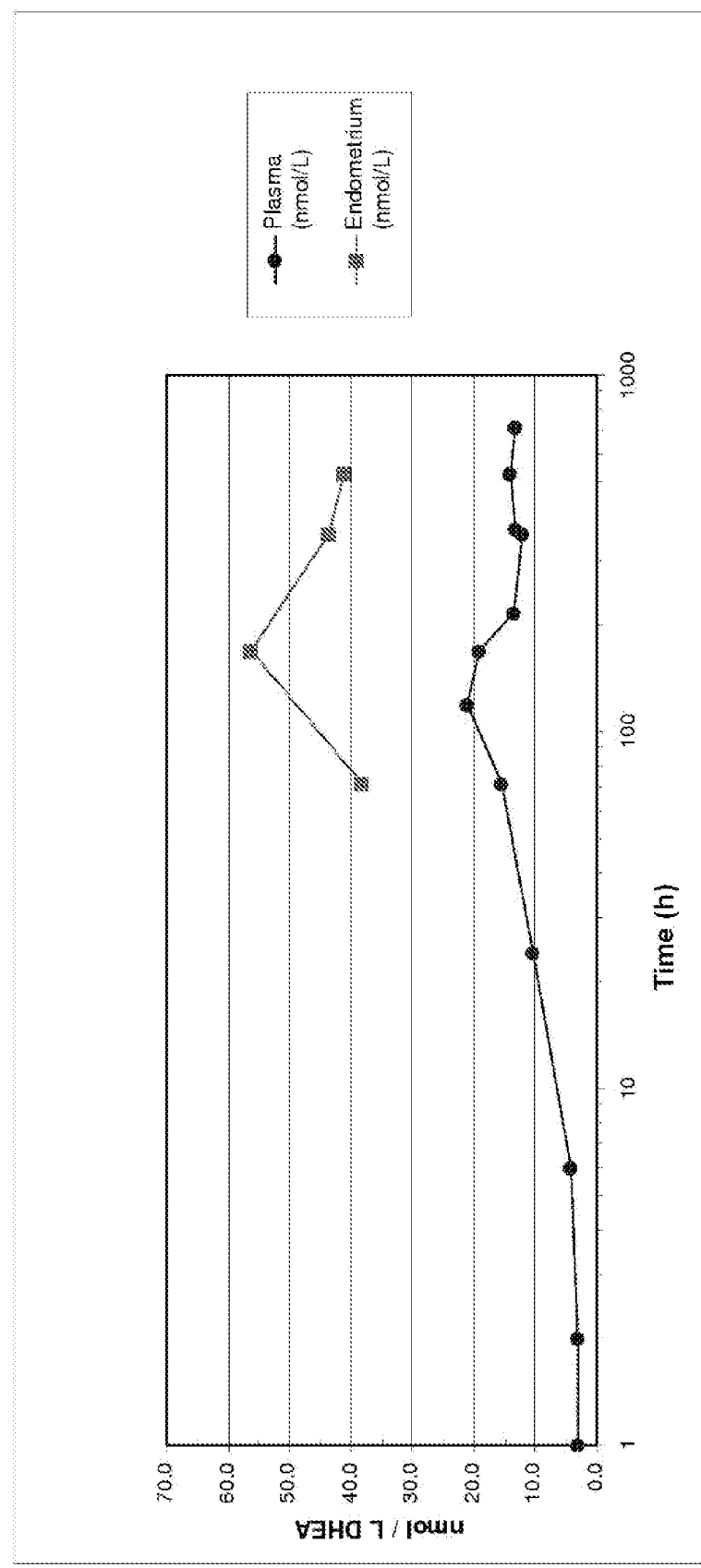
FIG. 11.—Levels of dehydroepiandrosterone (DHEA) in women plasma and endometrial fluid after administration of vaginal rings comprising 1.0 g of DHEA with no drug release modulating agent.

In FIG. 11 are shown plasma and endometrial levels of DHEA obtained after administration of rings with 1.0 g of DHEA without modulating agent. The amount of DHEA in the plasma was lower than in the endometrium with a maximum of approximately 20 nmol/L. DHEA levels in endometrium (squares) were markedly higher achieving values of 56.2 nmol/L. It was observed that plasma levels of DHEA tends to maintain constant after 216 hours (9 days) post-administration of the ring, achieving values close to 13 nmol/L.

Figure 12:
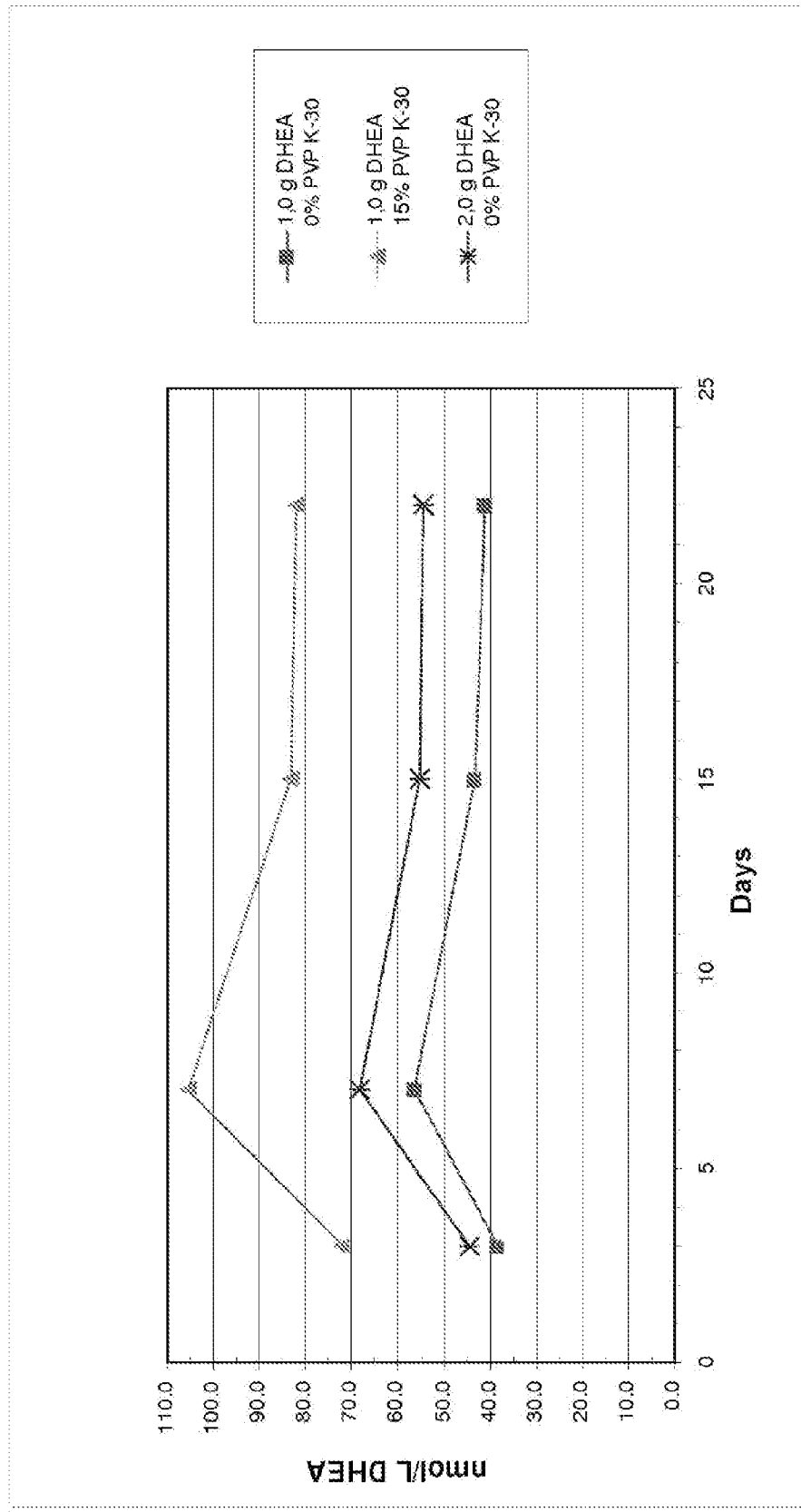
FIG. 12.—Levels of dehydroepiandrosterone (DHEA) in women endometrial fluid after administration of vaginal rings comprising 1.0 g and 2.0 g of DHEA with no PVP K-30 and 1.0 g of DHEA with 15% PVP K-30.

Endometrial DHEA levels obtained after administration of rings containing 1.0 g of DHEA and 15% PVP K-30 were higher than with rings without PVP K-30 at same doses of DHEA. In FIG. 12 this effect is clearly noted. When rings containing the modulating agent were administered, the DHEA amount found in the samples was in average 1.9 times higher (triangles) than with rings with no modulating agent (squares). Moreover, rings containing 1.0 g of DHEA with 15% PVP K-30 (triangles) induced an average increase of 1.5 times higher than that rings containing 2.0 g of DHEA with no modulating agent (crosses). In these results it was possible to distinguish a pick in DHEA levels in endometrium at 7 days post-administration of vaginal ring. It is likely that the peak does not occur precisely at this time, which may have pass unseen due to low number of samples of women endometrial fluid obtained over time. Even so, results are conclusive allowing stating that the amount of DHEA achieved in the endometrium with vaginal rings containing PVP K-30 was significantly higher than with rings not containing this agent, for both 1.0 g and 2.0 g DHEA rings. These results are similar with those obtained in the tests of in vitro release. The increase of DHEA in vitro release between days 5 to 30 (see FIG. 5) for rings containing 1.0 g of DHEA with 15% PVP K-30 when compared to rings without this agent was, in average, 1.8 times (versus 1.9 times in endometrium) and 1.6 times when compared to rings containing 2.0 g of DHEA with no PVP K-30 (versus 1.5 times in endometrium, FIG. 12). In other words, the levels obtained from vaginal rings in the endometrium could be projected from the amounts of DHEA that are obtained from in vitro release.

When measuring plasma DHEA levels, a different behavior to that seen in endometrial fluid was observed. On the one hand, plasma levels found with doses of 1.0 g of DHEA were higher for rings containing modifier PVP K-30 than for those not containing it (see FIG. 13, crosses versus circles), with an increase of 1.4 times; being consistent with the results obtained from in vitro release tests that gave differences of 1.8-fold between these two types of rings (see FIG. 5, dashed bars). On the other hand, for rings with 1.0 g of DHEA and 15% PVP K-30 could be predicted plasma levels 1.6 fold higher compared to the rings containing higher doses of DHEA (2.0 g) with no modifier, given its in vitro release behavior (FIG. 5, dotted bar 15% PVP K-30 versus white bar 0% PVP K-30); but the effect on plasma levels was reversed, as were higher for rings containing 2.0 g of DHEA than for rings with 1.0 g of DHEA and 15% PVP K-30 (FIG. 13, triangles versus crosses).

These results are completely unexpected and unpredictable, since from in vitro release was observed a higher release of DHEA in the presence of 15% PVP-K30 when compared to all DHEA doses without the agent. This did not allow projecting that with rings with PVP K-30 a higher DHEA tissue concentration would be obtained in vivo but with a lower plasma concentration when compared to rings without the agent and with higher doses of DHEA.

From the results of in vitro release was expected that at same DHEA concentration rings with PVP K-30 would provide a higher DHEA concentration than rings without PVP K-30, both at plasma and endometrial level, but surprising results have been obtained showing that with rings comprising PVP K-30, higher drug levels are achieved in the tissue in situ without increasing plasma concentrations in the same order, but not with the rings not containing PVP K-30.

Figure 13:
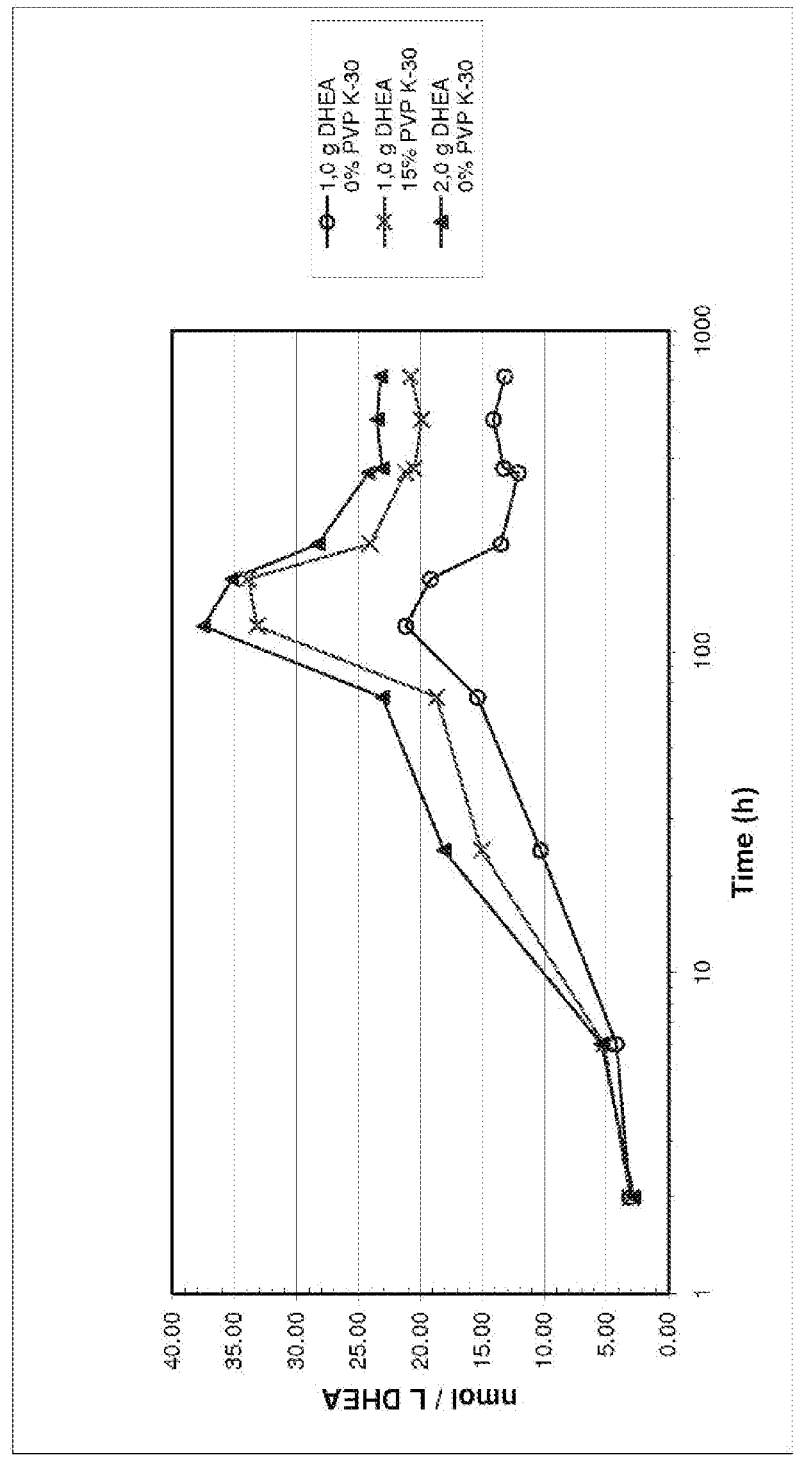
FIG. 13.—Levels of dehydroepiandrosterone (DHEA) in women plasma after administration of vaginal rings comprising 1.0 g and 2.0 g of DHEA with no PVP K-30 and 1.0 g of DHEA with 15% PVP K-30.

When increasing the amount of DHEA in the rings (without adding PVP K-30) in order to obtain higher concentrations in the endometrium, plasma drug concentration will also increase (FIG. 13). Therefore, to achieve greater tissue concentration without affecting plasma concentration in the same way is enough with co-administering DHEA and PVP in the ring without increasing DHEA dose in the same (FIG. 13).

Alternatively, the results found would suggest that vaginal rings containing other release-modulating agents, such as lactose, SLS and microcrystalline cellulose, are also useful to release DHEA into endometrium, since in vitro assays show that active agent is released in a sustained manner for at least 30 to 90 days. Furthermore, these agents also induced a higher DHEA release from the rings containing them during at least the first 15 to 22 days.

REFERENCES

Abdalla H and Thum M Y, 2004, An elevated basal FSH reflects a quantitative rather than qualitative decline of the ovarian reserve. Human Reprod 19: 893-898

Adams, 1985. Mol Cell Endocrinol 41:1-17

Alviggi C, Humaidan P, Howles C M, Tredway D, Hillier S G. 2009. Biological versus chronological ovarian age: implications for assisted reproductive technology. Reprod Biol Endocrinol 7:101

Battaglia D E et al., 1996, Influence of maternal age on meiotic spindle assembly in oocytes from naturally cycling women. Hum Reprod 11:2217-2222

Barad D H, Gleicher N. 2005. Increased oocyte production after treatment with dehydroepiandrosterone. Fertil Steril 84:756

Barad D, Gleicher N. 2006. Effect of dehydroepiandrosterone on oocyte and embryo yields, embryo grade and cell number in IVF. Human Reprod 21: 2845-2849

Barad D, Brill H, Gleicher N. 2007. Update on the use of dehydroepiandrosterone supplementation among women with diminished ovarian function. J Assist Reprod Genet 24: 629-634

Beral V. 2003. Breast cancer and hormone-replacement therapy in the Million Women Study. Lancet 362: 419-427

Broekmans F J, Soules M R, Fauser B C. 2009. Ovarian aging: mechanisms and clinical consequences. Endocr Rev 30:465-493

Broer S L, Mol B W, Hendriks D, Broekmans F J. 2009. The role of antimullerian hormone in prediction of outcome after IVF: comparison with the antral follicle count. Fertil Steril 91:705-714

Casson P R, Lindsay M S, Pisarka M D, Carson S A, Buster J E. 2000. Dehydroepiandrosterone supplementation augments ovarian stimulation in poor responders: a case series. Human Reprod 15: 2129-2132 de Vet A, Laven J S, de Jong F H, Temen A P N, Fauser B C. 2002. Antimullerian hormona serum levels: a putative marker for ovarian aging. Fertil Steril 77:357-62

Dehghani-Firouzabadi R, Tayebi N, Asgharnia M. 2008. Serum level of Anti-Mullerian Hormone in early follicular phase as a predictor of ovarian reserve and pregnancy outcome in assisted reproductive technology cycles. Arch Iranian Med 11:371-376

Durlinger A L et al., 2002. Regulation of ovarian function: the role of anti-Müllerian hormone. Reproduction 124: 601-609

Durlinger A L et al., 1999. Control of primordial follicle recruitment by anti-Müllerian hormone in the mouse ovary. Endocrinology 140:5789-5796

Durlinger A L et al., 2001. Anti-Müllerian hormone attenuates the effects of FSH on follicle development in the mouse ovary. Endocrinology 142:4891-4899

Evers J L, 2002, Female subfertility, Lancet 360:151-159

Fanchin R, Taieb J, Lozano D H, Ducot B, Frydman R, Bouyer J. 2005. High reproducibility of serum anti-Mullerian hormone measurements suggests a multi-staged follicular secretion and strengthens its role in the assessment of ovarian follicular status. Hum Reprod 20:923-927

Faddy M J, Gosden R G, Gougeon A, Richardson S J, Nelson J F. 1992. Accelerated disappearance of ovarian follicles in mid-life: implications for forecasting menopause. Hum Reprod 7:1342-1346

Faddy M J, Gosden R G, 1996. A model conforming the decline in follicle numbers to the age of menopause in women. Hum Reprod 11:1484-1486

Fanchin R, Schonäuer L M, Righini C, Guibourdenche J, Frydman R, Taieb J. 2003. Serum anti-Müllerian hormone is more strongly related to ovarian follicular status than serum inhibin B, estradiol, FSH and L H on day 3. Hum Reprod 18:323-327

Gleicher N, Ryan E, Weghofer A, Blanco-Mejia S, Barad D H. 2009. Miscarriage rates after dehydroepiandrosterone (DHEA) supplementation in women with diminished ovarian reserve: a case control study. Reprod Biol Endocrinol 7:108

Gleicher N, Weghofer A, Barad D H. 2010a. Improvement in diminished ovarian reserve after dehydroepiandrosterone supplementation. Reprod Biomed 21: 360-365

Gleicher N, Weghofer A, Barad D H. 2010b. Dehydroepiandrosterone (DHEA) reduces embryo aneuploidy: direct evidence from preimplantation genetic screening (PGS) supplementation. Reprod Biol Endocrinol 8:140

Gleicher N, Weghofer A, Barad D H. 2010c. Anti-Müllerian hormone (AMH) defines, independent of age, low versus good live-birth chances in women with severely diminished ovarian reserve. Fertil Steril 94: 2824-2827

Gougeon A. 1996. Regulation of ovarian follicular development in primates: facts and hypotheses. Endocrine Reviews 17:121-155

Hansen K R, Knowlton N S, Thyer A C, Charleston J S, Soules M R, Klein N A. 2008. A new model of reproductive aging: the decline in ovarian non-growing follicle number from birth to menopause, Hum Reprod 23:699-708

Hehenkamp W J, Looman C W, Themmen A P, de Jong F H, Te Velde E R, Broekmans F J. 2006. Anti-Müllerian hormone levels in the spontaneous menstrual cycle do not show substantial fluctuation. J Clin Endocrinol Metab 91:4057-4063

Heiss G, Wallace R, Anderson G L, Aragaki A, Beresford S A, Brzyski R, Chlebowski R T, Gass M, LaCroix A, Manson J E, Prentice R L, Rossouw J, Stefanick M L. 2008. Health risks and benefits 3 years after stopping randomized treatment with estrogen and progestin. JAMA 299:1036-1045

Hudson P L, Dougas I, Donahoe P K, Cate R L, Epstein J, Pepinsky R B, MacLaughlin D T, 1990. An immunoassay to detect human müllerian inhibiting substance in males and females during normal development. J Clin Endocrinol Metab 70:16-22

Hunt P A and Hassold T J, 2008, Human females meiosis: what makes a good egg go bad? Trends Genet 24:86-93

Kevenaar M E, Meerasahib M F, Kramer P, van de Lang-Born, de Jong F H, Groome N P, Themmen APN, Viseer J A, 2006. Serum anti-Müllerian hormone levels reflect the size of the primordial follicle pool in mice. Endocrinology 147: 3228-3234

Klinkert E R et al., 2005, Expected poor responders on the basis of an astral follicle count do not Benedit from a higher starting dose of gonadotrophins in IVF treatment: a randomized controlled trial. Hum Reprod 20:611-615

Kroboth P D, Salek F S, Pittenger A L, Fabian T J, Frye R F. 1999. DHEA and DHEA-S: a review. J Clin Pharmacol 39: 327-348

Kuliev A et al., 2005, Frequency and distribution of chromosome abnormalities in human oocytes. Cytogenet Genome Res 111:193-198

Labrie F. 1991. Intracrinology. Mol Cell Endocrinol 78: C113-C118

Labrie F, Bélanger A, Cusan L, Gomez J L, Candas B. 1997. Marked decline in serum concentrations of adrenal C19 sex steroid precursors and conjugated androgen metabolites during aging. J Clin Endocrinol Metab 82:2396-2402.

Labrie F, Bélanger A, Bélanger P, Bérubé R, Martel C, Cusan L, Gomez J, Candas B, Castiel I, Chaussade V, Deloche C, Leclaire J. 2006. Androgen glucuronides, instead of testosterone, as the new markers of androgenic activity in women. J Steroid Biochem Mol Biol 99:182-188.

Labrie F, Cusan L, Gomez J L, Côté I, Bérubé R, Bélanger P, Martel C, Labrie C. 2008. Effect of intravaginal DHEA on serum DHEA and eleven of its metabolites in postmenopausal women. J Steroid Biochem Mol Biol 111: 178-194.

Labrie F, Archer D, Bouchard C, Fortier M, Cusan L, Gomez J L, Girard G, Baron M, Ayotte N, Moreau M, Dubé R, Côté I, Labrie C, Lavoie L, Berger L, Gilbert L, Martel C, Balser J. 2009. Effect of intravaginal dehydroepiandrosterone (Prasterone) on libido and sexual dysfunction in postmenopausal women. Menopause 16:923-931.

Lee M M, Donahoe P K, Hasegawa T, Silverman B, Crist G B, Best S, Hasegawa Y, Noto R A, Schoenfeld D, MacLaughlin D T, 1996. Mullerian inhibiting substance in humans: normal levels from infancy to adulthood. J Clin Endocrinol Metab 81:571-576

Mamas L, Mamas E. 2009. Dehydroepiandrosterone supplementation in assisted reproduction: rationale and results. Curr Opin Obstet Gynecol 21: 306-308

Markström E, Svensson ECh, Shao R, Svanberg B, Billig H. 2002. Survival factors regulating ovarian apoptosis-dependence on follicle differentiation. Reproduction 123:23-30

McGee E A and Hhsueh A J. 2000. Inicial and cyclic recruitment of ovarian follicles. Endocr Rev 21:200-214

Munne S et al., 1995, Embryo morphology, developmental rates, and maternal age are correlated with chromosome abnormalities. Fertil Steril 64:382-391

Munne S et al., 2005, Preimplantation genetic diagnosis reduces pregnancy loss in women aged 35 years and older with a history of recurrent miscarriages. Fertil Steril 84: 331-335

Orentreich N, Brind J L, Rizer R L, Vogelman J H. 1984. Age changes and sex differences in serum dehydroepiandrosterone sulfate concentrations throughout adulthood. J Clin Endocrinol Metab 59:551-555.

Pellestor F et al., 2005, Effect of maternal age on the frequency of cytogenetic abnormalities in human oocytes. Cytogenet Genome Res 111:206-212

Scheffer G J, Broekmans F J, Dorland M, Habbema J D, Looman C W, to Velde E R, 1999. Antral follicle counts by transvaginal ultrasonography are related to age in women with proven natural fertility. Fertil Steril 72:845-851

Scheffer G J, Broekmans F J, Looman C W, Blankenstein M, Fauser B C, teJong F H, 2003. The number of antral follicles in normal women with proven fertility is the best reflection of reproductive age. Hum Reprod 18:700-706

Seifer D B, MacLaughlin D T, Christian B P, Feng B, Shelden R M. 2002. Early follicular serum müllerian-inhibiting substance levels are associated with ovarian response during assisted reproductive technology cycles. Fertil Steril 77:468-471

Sönmezer M, Ozmen B, Cil A P, Ozkavukçu S, Taş çi T, Olmuş H, Atabekoğlu C S. 2009. Dehydroepiandrosterone supplementation improves ovarian response and cycle outcome in poor responders. Reprod Biomed 19:508-513 te Velde E R and Pearson P L. 2002. The variability of female reproductive ageing. Human Reprod Update 8:141-154

Ueno S et al., 1989. Müllerian inhibiting substance in the adult rat ovary during various stages of the estrous cycle. Endocrinology 125:1060-1066

Van Disseldorp J, Faddy M J, Themmen A P, de Jong F H, Peeters P H, van der Schouw Y T, Broekmans F J. 2008. Relationship of serum antimullerian hormone concentration to age at menopause. J Clin Endocrinol Metab 93:2129-2134 van Houten ELAF, Themmen APN, Visser J A, 2010. Anti-Müllerian hormone (AMH): Regulator and marker of ovarian function. Annals d'Endocrinologie 71:191-197 van Rooij I A, Broekmans F J, Scheffer G J, Looman C W, Habbema J D, de Jong F H, Fauser B J, Themmen A P, te Velde E R. 2005. Serum antimullerian hormone levels best reflect the reproductive decline with age in normal women with proven fertility: a longitudinal study. Fertil Steril 83:979-987 van Rooij I A, Broekmans F J, te Velde E R, Fauser B C, Bancsi L F, de Jong F H, Themmen A P. 2002. Serum anti-Müllerian hormone levels: a novel measure of ovarian reserve. Hum Reprod 17:3065-3071 van Rooij I A, Tonkelaar I, Broekmans F J, Looman C W, Scheffer G J, de Jong F H, Themmen A P, te Velde E R. 2004. Anti-müllerian hormone is a promising predictor for the occurrence of the menopausal transition. Menopause 11:601-606

Visser J A et al., 2006. Anti-Müllerian hormone: a new marker for ovarian function. Reproduction 131:1-9

Wallace W H, Kelsey T W. 2010. Human ovarian reserve from conception to the menopause, PloS ONE 5(1): e87772

Wiser A, Gonen O, Ghetler Y, Shavit T, Berkovitz A, Shulman A. 2010. Addition of dehydroepiandrosterone (DHEA) for poor-responder patients before and during IVF treatment improves the pregnancy rate: A randomized prospective study. Human Reprod 25: 2496-2500.

The invention claimed is:

1. A sustained-release vaginal ring comprising 1% to 32% by weight, relative to the total weight of the formulation, of dehydroepiandrosterone as active agent, and 2% to 25% by weight, relative to the total weight of the formulation, of polyvinylpyrrolidone K-30 as modulator for active agent release.

2. The vaginal ring according to claim 1, wherein the active ingredient is released in a sustained manner for at least 90 days.

3. The vaginal ring according to claim 2, wherein it releases the active ingredient in a sustained manner for at least 60 days.

4. The vaginal ring according to claim 2, wherein it releases the active ingredient in a sustained manner for at least 30 days.

5. Method for increasing ovarian reserve in women comprising administering to women in need thereof the vaginal ring according to claim 1.

* * * * *